US012761210B2

(12) United States Patent
Hagel et al.

(10) Patent No.: US 12,761,210 B2

(45) Date of Patent: Oct. 13, 2026

(54) PREDICTING EFFICACY OF OR RESISTANCE TO TREATMENT OF COLON CANCER

(71) Applicant: 2cureX A/S, Copenhagen (DK)

(72) Inventors: Grith Hagel, Dragør (DK); Jacob Thastrup, Lillerød (DK); Ole Thastrup, Birkerød (DK)

(73) Assignee: 2cureX A/S, Copenhagen (DK)

(*) Notice: Subject to any disclaimer, the term of this patent is extended or adjusted under 35 U.S.C. 154(b) by 436 days.

(21) Appl. No.: 18/259,671

(22) PCT Filed: Dec. 28, 2021

(86) PCT No.: PCT/EP2021/087743

§ 371 (c)(1),
(2) Date: Jun. 28, 2023

(87) PCT Pub. No.: WO2022/144365

PCT Pub. Date: Jul. 7, 2022

(65) Prior Publication Data

US 2024/0069011 A1 Feb. 29, 2024

(30) Foreign Application Priority Data

Dec. 29, 2020 (EP) .................................... 20217599

(51) Int. Cl.
*G01N 33/50* (2006.01)
*C12N 5/09* (2010.01)

(52) U.S. Cl.
CPC ....... *G01N 33/5082* (2013.01); *C12N 5/0693* (2013.01); *G01N 33/5011* (2013.01); *C12N 2513/00* (2013.01); *G01N 2800/52* (2013.01)

(58) Field of Classification Search
None
See application file for complete search history.

(56) References Cited

FOREIGN PATENT DOCUMENTS

| | | | |
|---|---|---|---|
| CN | 1934273 | A | 3/2007 |
| CN | 102636648 | A | 8/2012 |
| EP | 3657167 | A1 | 5/2020 |
| WO | WO2019/122388 | A1 | 6/2019 |

OTHER PUBLICATIONS

Negrei, Carolina; et al; "Colon Cancer Cells Gene Expression Signature As Response to 5- Fluorouracil, Oxaliplatin, and Folinic Acid Treatment" Frontiers in Pharmacology, 7(172), 2016 (Year: 2016).*

Nagle, Peter W; et al; "Patient-derived tumor organoids for prediction of cancer treatment response" Seminars in Cancer Biology, 53, 258-264, 2018 (Year: 2018).*

Pasch, Cheri; et al; "Patient-Derived Cancer Organoid Cultures to Predict Sensitivity to Chemotherapy and Radiation" Clinical Cancer Research, 25, 5376-5387, 2019 (Year: 2019).*

Roy, P; et al; "Organoids as preclinical models to improve intraperitoneal chemotherapy effectiveness for colorectal cancer patients with peritoneal metastases: Preclinical models to improve HIPEC" International Journal of Pharmaceutics, 531, 143-152, 2017 (Year: 2017).*

Cercek, A. et al., Mismatch Repair-Deficient Rectal Cancer and Resistance to Neoadjuvant Chemotherapy, Clinical Cancer Research, 26: 3271-3279, Mar. 6, 2020.

Cristaldi, D. et al., A Reliable Flow-Based Method for the Accurate Measure of Mass Density, Size and Weight of Live 3D Tumor Spheroids, Micromachines, 11:465, 13 pages, Apr. 28, 2020, doi: 10.3390/mi11050465.

Finnberg, N. et al., Application of 3D tumoroid systems to define immune and cytotoxic therapeutic responses based on tumoroid and tissue slice culture molecular signatures, ONCOTARGET, 8(40): 66747-66757, Sep. 15, 2017.

Ganesh, K. et al., A rectal cancer organoid platform to study individual responses to chemoradiation, Nature Medicine, 25(10): 1607-1614, Oct. 1, 2019.

Jeppesen, M. et al., Short-term spheroid culture of primary colorectal cancer cells as an in vitro model for personalizing cancer medicine, PLOS One 12(9):e0183074, 19 pages, Sep. 6, 2017.

Ooft, S. et al., Patient-derived organoids can predict response to chemotherapy in metastatic colorectal cancer patients, Science Translational Medicine, 11, eaay2574, 10 pages, Oct. 9, 2019, DOI: 10.1126/scitranslmed.aay2574.

Ramzy, G. et al., Patient-Derived In Vitro Models for Drug Discovery in Colorectal Carcinoma, Cancers, 12, 1423, 21 pages, May 31, 2020, doi:10.3390/cancers12061423.

Wang, Q. et al., Design, synthesis and biological evaluation of a novel series of glycosylated platinum(iv) complexes as antitumor agents, Dalton Transactions, 45: 10366-10374, Jun. 21, 2016.

* cited by examiner

*Primary Examiner* — David W Berke-Schlessel
(74) *Attorney, Agent, or Firm* — Dinsmore & Shohl LLP; Weston R. Gould

(57) ABSTRACT

The invention relates to methods for predicting the efficacy and/or resistance to one or more treatment regimens comprising administration of a platinum compound in individuals suffering from colon cancer. The methods comprises providing a colon cancer biopsy from the individual, generating tumoroids thereof, and testing whether growth/viability/metabolism of said tumorids is inhibited by incubation with the platinum compounds.

20 Claims, 2 Drawing Sheets

PREDICTING EFFICACY OF OR RESISTANCE TO TREATMENT OF COLON CANCER

CROSS-REFERENCE TO RELATED APPLICATION

This application claims priority to co-pending PCT International Patent Application Serial No. PCT/EP2021/087743 filed Dec. 28, 2021, which claims priority to EP patent application No. 20217599.8 filed on Dec. 29, 2020, of which the entire content of both is incorporated herein by reference.

TECHNICAL FIELD

The present invention relates to the field of personalised medicine. More specifically, the invention relates to methods for predicting the efficacy of or the resistance to treatment of colon cancer with platinum compounds in individuals suffering from colon cancer.

BACKGROUND

For well over a decade, Genomic Precision Medicine has been the hope for patient-specific drug targeting of mutations in cancer patients. However, to date no convincing benefit from large scale tumor agnostic studies has been reported. The main causes include lack of availability of a matched targeted agent, poor response to a targeted agent despite matching, inability to combine most targeted agents because of toxicity, intra-tumor heterogeneity or mutations identified may not be 'drivers' of subsequent malignancy but are passengers and targeting them is futile.

There is thus an unmet clinical need for methods for predicting responsiveness of a given cancer patient to chemotherapy. Ooft et al., 2019 has described an in vitro based test based on patient-derived tumor organoids (PDOs). The PDOs were mechanically and enzymatically dissociated into single cells by incubation with TrypLE and replated to allow for formation of organoids, which were then incubated in the presence of various drugs. Whereas the test described by Ooft et al., 2019 predicted response to irinotecan-based therapies in more than 80% of patients, the test failed to predict the outcome for treatment with 5-fluorouracil plus oxaliplatin.

SUMMARY

There is thus an unmet need for in vitro based tests, which can predict the outcome of treatment with platinum compounds, such as oxaliplatin.

Surprisingly, the present invention provides a method for predicting the efficacy and/or resistance to treatment of colon cancer with platinum compounds. In contrast to prior art methods, the methods of the invention can be used to predict said efficacy and/or resistance with high accuracy. The invention shows that inhibition of growth of tumoroids from colon cancer patients in vitro in the presence of test compounds or combinations of test compounds, can be used to predict efficacy and/or resistance to said test compounds (in particular platinum compounds) or combinations thereof in said colon cancer patients on an individual level. Interestingly, the methods of the invention in some embodiments rely on preparation of tumoroids from tissue fragments comprising a plurality of cells attached to each other. Thus, in some embodiments in contrast to prior art methods, the methods of the invention may allow a plurality of cells to maintain attached to each other throughout the methods. Furthermore, the methods of the invention in some embodiments rely on determining inhibition of growth by determining the size of tumoroids. Thus, in contrast to prior art methods, in some embodiments the methods of the invention determines inhibition of growth by determining size of tumoroids instead of determining activity by measuring ATP levels. Interestingly, the present invention shows that inhibition of growth of tumorids more accurately can be used in predicting efficacy or resistance. Without being bound by theory it is believed that use of determination of growth inhibition of tumoroids more accurately reflects in vivo sensitivity, because such methods are much more sensitive as shown by the present invention.

The invention is further described below, and defined in the claims attached hereto.

DETAILED DESCRIPTION

Definitions

Figure 1:
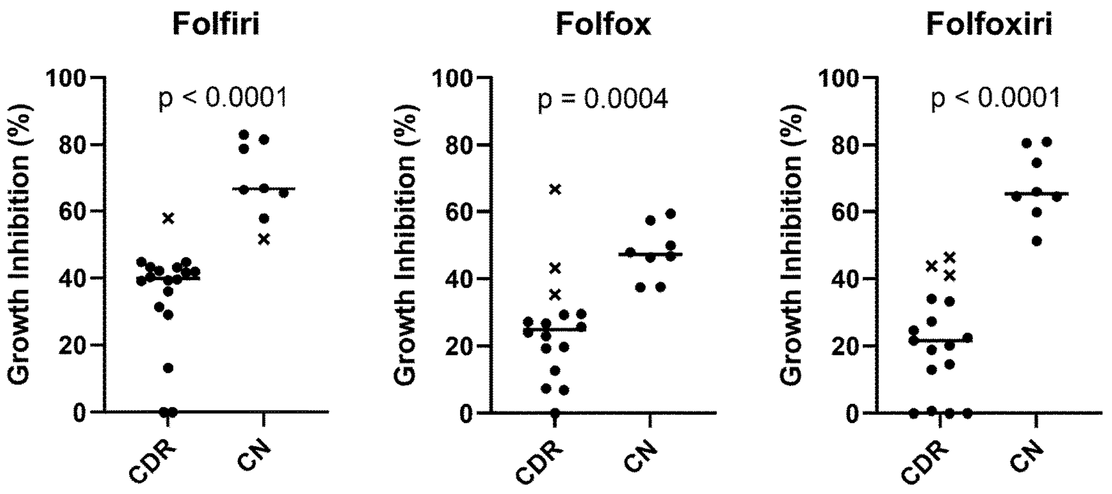
FIG. 1 shows growth inhibition values plotted for each patient group and drug regimen. Each symbol represents a patient result, the horizontal lines are the mean value. Growth inhibition grouping was performed by k-mean clustering. X symbols indicate patients that group with the opposite patient group. CDR: Clinical drug resistant patients, CN: Chemonaive patients.

The term "colon cancer biopsy" as used herein refers to a sample obtained from an individual suffering from colon cancer, wherein said sample comprises or consists of colon cancer tissue. Said colon cancer tissue may be from the primary colon cancer, from lymph nodes or from one or more metastases of said colon cancer. Said biopsy may for example be a needle biopsy, fine needle biopsy, and/or a surgical biopsy.

The term "colon cancer" refers to cancers, which have arisen in the colon. Accordingly, term "colon cancer" as used herein does not include rectal cancers. The colon cancer may be of any histologic type, including but not limited to malignant epithelial tumours. Malignant epithelial tumours of the colon may be divided into five major histologic types: adenocarcinoma, mucinous adenocarcinoma (also termed colloid adenocarcinoma), signet ring adenocarcinoma, scirrhous tumours and carcinoma simplex. Colon cancer may be staged using any of several classification systems known in the art. The Dukes system is one of the most often employed staging systems. See Dukes and Bussey 1958 (Br J Cancer 12: 309). The colon cancer may be of any of the aforementioned types or classes.

The term "comprising" should be understood in an inclusive manner. Hence, by way of example, a composition comprising compound X, may comprise compound X and optionally additional compounds.

The term "growth" as used herein in relation to tumoroid, preferably refers to an increase in size, i.e. an increase in area, volume and/or mass of the tumoroids. Said area is preferably the projected area, such as the largest projected area.

The term "platinum compound", as used herein refers to a compound comprising an electrostatically neutral platinum coordination complex. Preferably, the platinum compound comprises either a square planar or an octahedral platinum complex, more preferably, the platinum compound may be a square planar Pt(II) compound or an octahedral Pt(IV) compound.

The term "sol-gel" as used herein refers to a support, which reversibly can shift between a "sol-state" and a "gel-state". It can be determined whether a support is in the "sol-state" or "gel-state" by placing the support in a conventional test tube. When the test tube is turned upside down, in the case where the interface (meniscus) between the support and air is deformed (including a case wherein the solution flows out from the test tube) due to the weight of the solution per se, the support is defined as being in the "sol state". On the other hand, in a case where the interface (meniscus) between the solution and air is not deformed due to the weight of the solution per se, even when the test tube is turned upside down, the above support is defined as being in the "gel state".

The term "plurality" should be understood as "at least two".

The term "tissue fragment" as used herein refers to a fragment of a biopsy comprising a plurality of cells (e.g. cancer cells) attached to each other. In general, "tissue fragments" according to the invention are fragments of a colon cancer biopsy.

The term "tumoroid" as used herein refers to a plurality of cells attached to each other, obtained after cultivating a tissue fragment comprising cancer cells in vitro. Preferably, a tumoroid comprises at least 10 cells, such as at least 50 cells, for example at least 100 cells attached to each other. Frequently, the tumoroid is essentially ball-shaped in which case, they may also be referred to as "spheroids". However, tumoroids may also adopt other 3D shapes.

The term "treatment" as used herein may refer to preventive, curative or ameliorating treatment. Thus, "treatment" imparts a benefit to a subject afflicted with a disease or at risk of acquiring a disease, including improvement in the disease in the subject (e.g., in one or more symptoms), delay in the progression of the disease, disorder or condition, prevention or delay of the onset of the disease.

Method

It is one aspect of the invention to provide methods for predicting the efficacy of treatment of colon cancer with one or more different treatments in an individual suffering from said cancer, wherein each treatment is treatment with a platinum compound and optionally one or more additional anti-cancer compounds, said method comprising the steps of

- providing at least one colon cancer biopsy obtained from said individual,
- dissociating the biopsy into single cells; or tissue fragments each comprising a plurality of cells attached to each other,
- incubating said tissue fragments in a cell-compatible support, which supports 3 dimensional maintenance and/or growth of human or other mammalian cells to generate tumoroids,
- incubating a random selection of said tumoroids with the platinum compound (and additional anti-cancer compound(s)) of each treatment under conditions supporting 3 dimensional maintenance and/or of human or other mammalian cells
- determining whether growth/viability/metabolism (preferably growth) of said tumoroids is inhibited by incubation with said platinum compound (and additional anti-cancer compound(s)),
- wherein inhibition of growth of said tumoroids by a platinum compound (and additional anti-cancer compounds) of a given treatment is indicative of efficacy of said treatment of colon cancer in said individual. Alternatively, but less preferably, inhibition of viability and/or metabolism may be indicative of efficacy.

The individual suffering from said cancer may be any individual. Typically, the individual is mammal, for example a human being, a cat, a dog or a horse. Preferably, the individual is a human being.

The invention also provides methods for predicting resistance to treatment with one or more different treatments of colon cancer in an individual suffering from said cancer, wherein each treatment is treatment with a platinum compound and optionally one or more additional anti-cancer compounds, said method comprising the steps of

- providing at least one colon cancer biopsy obtained from said individual,
- dissociating the biopsy into single cells; or tissue fragments each comprising a plurality of cells attached to each other,
- incubating said tissue fragments in a cell-compatible support, which supports 3 dimensional maintenance and/or growth of human or other mammalian cells to generate tumoroids,
- incubating a random selection of said tumoroids with the platinum compound (and additional anti-cancer compound(s)) of each treatment under conditions supporting 3 dimensional maintenance and/or growth of human or other mammalian cells
- determining whether said tumoroids are capable of growth and/or whether there is a decrease in viability and/or metabolism during incubation with said platinum compound (and additional anti-cancer compound(s)),
- wherein growth of said tumoroids by a platinum compound (and additional anti-cancer compounds) of a given treatment is indicative of resistance to said treatment of colon cancer in said individual. Alternatively, but less preferably, no decrease in viability and/or metabolism may be indicative of resistance.

The brackets ( ) indicate that the subject matter within the brackets is optional. Thus, said incubation of the tumoroids may be incubation with a platinum compound or a platinum compound and one or more additional anti-cancer compounds depending on whether the treatment is treatment with a platinum compound only or the treatment is a combination treatment with a platinum compound and one or more additional anti-cancer compounds.

The methods are useful for simultaneous testing of more than one different treatment. Thus, the methods may be used for testing at least 2, for example at least 5, such as at least 10 different treatments, wherein each treatment is either treatment with a platinum compound alone or treatment with a combination of a platinum compound and one or more additional anti-cancer compounds. In addition to testing treatment with said platinum compounds, the methods may also involve parallel testing of treatments. Whereas there in principle is no upper limit to the number of different treatments to be tested, most frequently, at the most 2000, such as at the most 1000, for example at the most 500, such as at the most 100 different treatments are tested.

In some embodiments only in the range 1 to 5, such as in the range of 1 to 3 different treatments are tested. For example, the methods may involve testing only of the combinations of compounds which are standard of care of colon cancer.

The invention further provides methods of identifying a platinum compound, which alone or in combination with one or more additional anti-cancer compounds are likely to be efficient in treatment of colon cancer in an individual in need thereof, said method comprising the steps of providing at least one colon cancer biopsy obtained from said individual, dissociating the biopsy into single cells; or tissue fragments each comprising a plurality of cells attached to each other, incubating said tissue fragments in a cell-compatible support, which supports 3 dimensional maintenance and/or growth of human or other mammalian cells to generate tumoroids, providing a plurality of test combinations, wherein each test combination comprises a platinum compound and optionally one or more additional componds incubating individual random selections of said tumoroids with each of the test combinations under conditions supporting 3 dimensional maintenance and/or growth of human or other mammalian cells determining whether growth/viability/metabolism of said tumoroids is inhibited by incubation with said test combinations, wherein inhibition of growth of said tumoroids by a given test combination is indicative of efficacy of treatment of colon cancer in said individual with the platinum compound (and additional anti-cancer compounds) of said test combination.

Alternatively, but less preferably, inhibition of viability and/or metabolism may be indicative of efficacy.

The methods may be used for testing a plurality of test combinations, e.g. at least 2, for example at least 5, such as at least 10 different test combinations, wherein each test combination is either a platinum compound alone or a combination of a platinum compound and one or more additional anti-cancer compounds. Whereas there in principle is no upper limit to the number of different treatments to be tested, most frequently, at the most 2000, such as at the most 1000, for example at the most 500, such as at the most 100 different treatments are tested.

The invention furthermore provides methods of treatment of an individual suffering from colon cancer, said method comprising the steps of identifying a platinum compound, which alone or in combination with one or more additional anti-cancer compounds is likely to be efficient in treatment of colon cancer in said individual by the methods described herein administering said identified platinum compound or combination of platinum compound with one or more additional anti-cancer compounds to said individual thereby treating said colon cancer.

Colon Cancer

Surprisingly the invention shows that inhibition of growth/viability/metabolism of tumoroids from colon cancer patients in vitro in the presence of test compounds, can be used to predict efficacy and/or resistance to said test compounds. In particular, the invention shows that inhibition of growth of tumoroids from colon cancer patients in vitro in the presence of test compounds, can be used to predict efficacy and/or resistance to said test compounds in said individual with high accuracy.

The colon cancer may be any cancer, which has arisen in the colon. Thus, the colon cancer may be any cancer, where the primary tumour is situated in the colon. The colon cancer may be a metastatic colon cancer, in which case metastases may be found in other locations of the affected individual apart from the colon.

The methods comprise providing at least one, such as in the range of 1 to 10 colon cancer biopsies obtained from an individual suffering from colon cancer. Each of said biopsies should comprise or preferably even consist of colon cancer tissue. Said colon cancer tissue may be from the primary tumour or from one or more different metastases.

The biopsy may be taken by any suitable means, e.g. it may be a needle biopsy, a fine needle biopsy, and/or a surgical biopsy or a combination of the aforementioned.

Platinum Compound

Interestingly, the invention shows that inhibition of growth/viability/metabolism of tumoroids from colon cancer patients in vitro, can be used to predict efficacy and/or resistance to platinum compounds alone or in combination with other anti-cancer compounds. In particular, the invention shows that inhibition of growth of tumoroids from colon cancer patients in vitro in the presence of platinum compounds, can be used to predict efficacy and/or resistance to said platinum in said individual with high accuracy. Said anti-cancer compounds may for example be any of the compounds described below in the section “Anti-cancer compound”.

The platinum compound may be any cytotoxic compound comprising an electrostatically neutral platinum coordination complex. In particular, the platinum compound may be any compound comprising an electrostatically neutral platinum coordination complex used in cancer treatment.

Preferably, the platinum compound comprises either a square planar or an octahedral platinium complex, more preferably, the platinum compound may be a square planar Pt(II) compound or an octahedral Pt(IV) compound. More preferably, said square planar or octahedral platinium complex has two donor groups that are either primary or secondary amines. These amine ligands are preferably either two cis monodentate ligands or one bidentate chelating ligand. Furthermore, it is preferred that said square planar or octahedral platinium complex has two donor groups that can act as leaving groups. Said donors may in particular be either Cl or O, and can be either two monodentate or one bidentate ligand. In general "platinum compounds" are cytotoxic. Non-limiting examples of platinum compounds include, but are not limited to carboplatin, cis-platin, cisplatinum, oxaliplatin or satraplatin.

In preferred embodiment the platinum compound is oxaliplatin.

The platinum compounds may be delivered to patients in free form or by using any suitable delivery vehicles. Accordingly, the platinum compounds to be used with the methods of the invention may for example be in free form or it may be associated with any suitable delivery vehicle. Non-limiting examples of such are e.g. Aroplatin, Lipoplatin or ProLindac.

As noted above, the methods may be used for parallel testing of several combinations of compounds. In such cases it is preferred that at least one combination of compounds tested comprise a platinum compound selected from the group consisting of carboplatin, cisplatin, oxaliplatin or satraplatin. In some embodiments, several or even all combinations comprise a platinum compound selected from the group consisting of carboplatin, cisplatin, oxaliplatin or satraplatin alone and/or in different combinations with other anti-cancer compounds. Preferably said platinum compound is oxaliplatin.

In one embodiment the methods comprise or consist of predicting efficacy of and/or resistance to Folfox in an individual suffering from colon cancer. In such embodiments, the method comprises incubating said tumoroids in the presence of fluorouracil (5-FU), oxaliplatin and folinic acid and determining whether growth/viability/metabolism, preferably determining whether growth of the tumoroids is inhibited.

In one embodiment the methods comprise or consist of testing efficacy of and/or resistance to Folfoxiri in an individual suffering from colon cancer. In such embodiments, the method comprises incubating said tumoroids in the presence of fluorouracil (5-FU), oxaliplatin, irinotecan or a metabolite thereof and folinic acid and determining whether growth/viability/metabolism, preferably determining whether growth of the tumoroids is inhibited. Said metabolite of irinotecan may e.g. be SN38.

Anti-Cancer Compound

The anti-cancer compounds to be used with the methods of the present invention may be any compound with anti-cancer effect. For example, it may be any active compound used in the treatment of cancer. Preferably, the anti-cancer compound is a compound useful in the treatment of colon cancer.

The following provides non-limiting examples of anti-cancer compounds, however, the methods can be used for predicting the efficacy of or resistance to any anti-cancer compound when used in combination with a platinum compound.

In one embodiment at least one additional anti-cancer compound is a fluoropyrimidine, for example a fluoropyrimidine selected from the group consisting of 5-fluorouracil (5-FU), capecitabine and tegafur.

In one embodiment at least one additional anti-cancer compound is a taxane, for example a taxane selected from the group consisting of taxol and docetaxel.

In one embodiment at least one additional anti-cancer compound is a PARP inhibitor, for example a PARP inhibitor selected from the group consisting of olaparib, rucaparib, niraparib, talazoparib, veliparib and pamiparib.

In one embodiment at least one additional anti-cancer compound is an immune checkpoint inhibitor, for example an immune checkpoint inhibitor selected from the group consisting of inhibitors of CTLA4, PD-1 and PD-L1.

In one embodiment at least one additional anti-cancer compound is an antibody, for example an antibody selected from the group consisting of cetuximab, bevacizumab, panitumumab, ramucirumab and necitumumab.

In some embodiments the methods do not comprise testing efficacy and/or resistance to an anti-cancer compound, which is irinotecan or SN38.

Concentration of Platinum Compounds and Anti-Cancer Compounds

The methods of the invention comprises a step of incubating tumoroids with platinum compounds and optionally one or more additional compounds.

Any useful concentration of said compounds may be used. The skilled person will be able to identify a useful concentration. A useful concentration is a concentration at which growth/viability/metabolism of tumoroids from sensitive colon cancer patients is inhibited, whereas growth/viability/metabolism of tumoroids from resistant colon cancer patients is not inhibited. Preferably, growth is used for identifying a useful concentration. A useful concentration may be determined by determining the $ED_{50}$ in respect of inhibition of growth and/or viability and/or metabolism. $ED_{50}$ in respect of growth may for example be determined as described in Example 2 below.

In respect of platinum compounds, the concentration may typically be in the range of 0.4 to 150 μM, for example in the range of 0.4 to 100 μM, such as in the range of 0.4 to 50 μM, for example in the range of 0.4 to 20 μM, such as in the range of 0.4 to 10 μM. This may in particular be the case, when the platinum compound is oxaliplatin.

In one embodiment, the methods comprise or consist of predicting efficacy of and/or resistance to Folfox in an individual suffering from colon cancer. In said embodiment, the concentrations may be in the range of 0.1 to 20 μM, for example in the range of 1 to 20 μM, such as in the range of 5 to 10 μM 5-FU, in the range of 0.4 to 20 μM, such as in the range of 0.4 to 10 μM, for example in the range of 2 to 7 μM oxaliplating and/or in the range of 0.1 to 20 μM, for example in the range of 1 to 20 μM, such as in the range of 5 to 10 μM folinic acid.

In one embodiment the methods comprise or consist of testing efficacy of and/or resistance to Folfoxiri in an individual suffering from colon cancer. In such embodiments, the concentrations may be in the range of 0.1 to 20 μM, such as in the range of 0.5 to 5 μM 5-FU, in the range of 0.4 to 20 μM, such as in the range of 0.4 to 10 μM, for example in the range of 0.4 to 1 μM oxaliplating and/or in the range of 0.1 to 20 μM, such as in the range of 0.5 to 5 μM folinic acid.

Tissue Fragments

The methods of the invention comprises providing at least one colon cancer biopsy and cultivating tumoroids from said biopsy.

In general this requires a step of dissociating the biopsy into single cells; or tissue fragments. In some embodiments, the biopsy may be dissociated into single cells. However, in preferred embodiments the biolsy is dissociated into tissue fragments. It is important that each of said tissue fragments comprise a plurality of cells attached to each other. In some embodiments it is thus important that the biopsy is not dissociated into single cells.

The step of dissociation may be done by mechanical means, e.g. by cutting, shearing or otherwise mechanically subdividing. It may also be done by enzymatic treatment, or it may be done by a combination of both.

Cutting may involve removal of parts of the biopsy, which visibly do not comprise useful tumor tissue, for example removal of visible fatty areas and/or visible necrotic areas.

The dissociation may further comprise incubation with one or more enzymes. It is important that said incubation is performed in a manner, so that the biopsy is not dissociated to single cells. For example, the enzyme may be a proteolytic enzyme, preferably a proteolytic enzyme capable of cleaving peptide bonds between glycine and proline of a Pro-X-Gly-Pro sequence. In particular, the enzyme may be collagenase. In some embodiments it is preferred that only one enzyme is added to the biopsy and/or the tissue fragments, and preferably said one enzyme is collagenase.

Whereas the dissociation may comprise incubation with a proteolytic enzyme, it is preferred that said proteolytic enzyme is not too aggressive. It is thus preferred that the enzyme is not a proteolytic enzyme specifically cleaving peptide bonds on the C-terminal side of lysine and arginine. More preferably, it is preferred that a proteolytic enzyme specifically cleaving peptide bonds on the C-terminal side of lysine and arginine is not added to said biopsy, to said tissue fragments or to said tumoroids at any time during the procedure. Examples of proteolytic enzymes specifically cleaving peptide bonds on the C-terminal side of lysine and arginine include trypsin and TrypLE.

As noted above, the biopsy is preferably dissociated into tissue fragments each comprising a plurality of cells attached to each other. Thus, the tissue fragments may be aggregates of cells. In general the tissue fragments have a diameter of at least 30 μm.

It is preferred that the majority of the tissue fragments, for example at least 50%, such as at least 70%, for example at least 90% of the tissue fragments comprise at least 10 cells attached to each other, such as in the range of 10 to 50 cells attached to each other.

As noted above, in some embodiments, it is preferred that the method does not contain a step of dissociating the biopsy into single cells. In some embodiments, it is also preferred that the method does not contain a step of dissociating the tissue fragments into single cells. In some embodiments, tt is also preferred that the method does not contain a step of dissociating the tumoroids into single cells. In fact, it is preferred that the method does not contain a step of dissociating the tumoroids obtained into smaller fragments.

In embodiments where the biopsy is dissociated into single cells, said single cells are preferably cultivated in a manner allowing them to form tumoroids.

Cultivating Tumoroids

The method according to the invention comprise steps of incubating tissue fragments in a cell-compatible support, which supports 3 dimensional maintenance and/or growth of human or other mammalian cells, thereby generating tumoroids. The tumoroids are 3 dimensional structures of a plurality of cells attached to each other obtained after cultivating tissue fragments comprising cancer cells.

The methods also comprise steps of incubating the tumoroids thus obtained in a cell-compatible support, which supports 3 dimensional maintenance and/or growth of human cells. In general, a number of tumoroids are randomly selected and incubated in a cell-compatible support in a separate manner, e.g. in physically separated spaces, e.g. in different containers, wells or compartments. Each group of randomly selected tumoroids are incubated with a different combination of test compounds (i.e. different combinations of either a platinum compound or a platinum compound and one or more additional anti-cancer compounds.

Cell-Compatible Support

In a preferred embodiment the cell-compatible support, is a support that reversible can change between a sol-state and a gel-stat. Thus, the cell-compatible support may be a sol-gel capable of supporting growth of human or other mammalian cells.

The term "cell compatible" as used herein refers to that the support when being in contact with cellular systems do not produce an adverse effect on the cells.

The support should preferably be able to support maintenance and/or 3 dimensional maintenance and/or growth of cells. A support is capable of supporting maintenance and/or 3 dimensional maintenance and/or growth of cells, if cells can reside in contact with said support and either stay alive and/or proliferate.

In particular, the support may be a support capable of supporting growth of 3D cell cultures. Typically 3D cultures are embedded in a polymer, for example a hydrogel like Matrigel (BD Matrigel™), PuraMatrix™ (3D Matrix Medical Technology), alginate or gelatin that upon a temperature change can shift between a sol-state and a gel-state without major disturbance to embedded cells.

It is preferred that the support is a temperature reversible gel, i.e. a gel, which reversible can change between the sol-state and the gel-state dependent on the temperature.

In particular it is preferred that the support is a cell compatible sol-gel.

Frequently, the support comprises one or more polymers. For example the sol-gel may comprise or consist of a hydrogel, e.g. a cell compatible hydrogel. The sol-gel may also be a mixture of different hydrogels.

A hydrogel according to the present invention generally consists of one or more polymers and a dispersion liquid. Said polymer(s) are herein referred to as "hydrogel polymers". The hydrogel polymer may be a polymer, which has a crosslinking or network structure, and has a property such that it can form a hydrogel by retaining water (in the inside thereof) on the basis of such a structure. The hydrogel may also comprise a combination of two or more different hydrogel polymers. Further, the term "hydrogel" refers to a gel which comprise, at least a crosslinked or network structure comprising a hydrogel polymer, and a dispersion liquid supported or retained by such a structure.

The "dispersion liquid" is typically an aqueous liquid useful for cultivation of cells. Thus, the dispersion liquid may be a cell cultivation medium. Cell cultivation media comprises the compounds required for maintenance and/or growth of cells, such as nutrients, hormones and growth factors. The cell cultivation medium should be compatible with colon cancer cells. The skilled person will be able to select a useful cell cultivation medium, which for example may be stem cell medium. In particular, the support may be a sol-gel, which reversibly can switch between the "sol state", and the "gel state". Different factors may influence whether the sol-gel is in the "sol-state" or the "gel-state". Thus, for example the state of the sol-gel may be dependent on pH, temperature or the presence of specific ions.

In one embodiment the state of the sol-gel is dependent on pH. Thus, at a pH above a given pH the sol-gel may be in the gel-state, whereas at pH below a given pH the sol-gel may be in the sol-state. It is also possible that at a pH above a given pH the sol-gel may be in the sol-state, whereas at pH below a given pH the sol-gel may be in the sol-state. A non-limiting example of such a sol-gel includes Puramatrix gel available from BD Biosciences.

It is also comprised within the invention that the sol-gel may be in the gel-state, above a certain concentration of a compound, for example above a certain concentration of an ion. Said ion may for example be selected from the group consisting of $Ca^{2+}$ and $Na^{+}$.

In a preferred embodiment of the invention the sol-gel changes between the sol-state and the gel-state based on temperature. Thus, the sol-gel, may be a sol-gel, which reversibly can switch between the "sol state", and the "gel state" at the "sol-gel transition temperature".

The state of a sol-gel transition may preferably be determined as follows. 1 ml of a sol-gel in a sol state is poured into a test tube having an inside diameter of 1 cm, and is left standing for a predetermined time, e.g. 12 hours. Thereafter, when the test tube is turned upside down, in the case where the interface (meniscus) between the sol-gel and air is deformed (including a case wherein the solution flows out from the test tube) due to the weight of the solution per se, the above sol-gel is defined as a "sol state". On the other hand, in a case where the interface (meniscus) between the sol-gel and air is not deformed due to the weight of the solution per se, even when the test tube is turned upside down, the above sol-gel is defined as a "gell state".

The state of the sol-gel may be determined at particular temperatures, to determine the sol-gel transition temperature, at different pH or using other varying conditions.

The sol-gel transition temperature may be determined by performing above method while gradually increasing the above "predetermined temperature" (e.g., in 1 degrees C. increment), and determining the temperature at which the "sol state" is converted into the "gel state".

Determination and measurement of the "sol state," "gel state," and "sol-gel transition temperature" may also be carried out as mentioned below according to the definition and method described in a publication (H. Yoshioka et al., Journal of Macromolecular Science, A31(1), 113 (1994)).

That is, the dynamic elastic modulus of a sample at an observed frequency of 1 Hz is determined by gradually shifting the temperature from a low temperature side to a high temperature side (1 degrees C.1 min). In this measurement, the sol-gel transition temperature is defined as a temperature at which the storage elastic modulus (G', elastic term) of the sample exceeds the loss elastic modulus (G", viscous term). In general, the sol state is defined as a state in which G">G' is satisfied, and the gel state is defined as a state in which G"<G' is satisfied. A method of measuring elastic modulus, is e.g. described in: "Modern Industrial Chemistry" (Kindai Kyogyo Kagaku) No. 19, edited by Ryohei Oda, et al., Page 359, published by Asakura Shoten, 1985).

It is preferred that the support to be used with the present invention is a sol-gel with a sol-gel transition temperature in the range of 0 to 35° C., such as in the range 5 to 35° C., for example in the range of 10 to 35° C.

The sol-gel may for example be selected from the group consisting of gelatinous gels and copolymers.

The support may in particular be a sol-gel, and said sol-gel may for example be a hydrogel. The hydrogel usable for the support according to the present invention is not particularly limited, however preferably hydrogel exhibits the above-mentioned reversible sol-gel transition, such as a thermo reversible sol-gel transition (that is, preferably it has a sol-gel transition temperature).

Specific non-limiting examples of the hydrogel polymers includes e.g., polyalkyleneoxide block copolymer represented by block copolymers comprising polypropylene oxide portions and polyethylene oxide portions; etherified (or ether group-containing) celluloses such as methyl cellulose and hydroxypropyl cellulose; chitosan derivatives, e.g. such as described by K. R. Holme. et al. Macromolecules, 24, 3828 (1991).

The hydrogel polymer may preferably comprise a combination of plural hydrophobic blocks having a cloud point, and a hydrophilic block bonded thereto. The hydrophobic block may comprise or consist of hydrophobic monomers, whereas the hydrophilic block may comprise or consist of hydrophilic monomers. The cloud point based on the hydrophobic bonds preferably corresponds to the above-mentioned sol-gel transition temperature of the hydrogel.

More specifically, such a polymer having a cloud point may be one selected from the group consisting of: polypropylene oxide, copolymers comprising propylene oxide and another alkylene oxide, poly N-substituted acrylamide derivatives, poly N-substituted methacrylamide derivatives, copolymers comprising an N-substituted acrylamide derivative and an N-substituted methacrylamide derivative, polyvinyl methyl ether, and partially-acetylated product of polyvinyl alcohol.

Specific examples of the poly N-substituted acrylamide derivatives and poly N-substituted methacrylamide derivatives includes e.g. Poly-N-acryloyl piperidine, Poly-N-n-propyl methacrylamide, Poly-N-isopropyl acrylamide, Poly-N,N-diethyl acrylamide, Poly-N-isopropyl methacrylamide, Poly-N-cyclopropyl acrylamide, Poly-N-acryloyl pyrrolidine, Poly-N,N-ethyl methyl acrylamide, Poly-N-cyclopropyl methacrylamide or Poly-N-ethyl acrylamide.

Specific examples of the above hydrophilic monomer may include: N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinyl sulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. However, the hydrophilic monomer to be usable in the present invention is not restricted to these specific examples.

Specific examples of the above hydrophobic monomer may include: acrylate derivatives and methacrylate derivatives such as ethyl acrylate, methyl methacrylate, and glycidyl methacrylate; N-substituted alkyl methacrylamide derivatives such as N-n-butyl methacrylamide; vinyl chloride, acrylonitrile, styrene, vinyl acetate, etc. However, the hydrophobic monomer to be usable in the present invention is not restricted to these specific examples.

Specific examples of the hydrophilic block to be combined with (or bonded to) the above-mentioned block having a cloud point may include: methyl cellulose, dextran, polyethylene oxide, polyvinyl alcohol, poly N-vinyl pyrrolidone, polyvinyl pyridine, polyacrylamide, polymethacrylamide, poly N-methyl acrylamide, polyhydroxymethyl acrylate, polyacrylic acid, polymethacrylic acid, polyvinyl sulfonic acid, polystyrene sulfonic acid, and salts of these acids; poly N,N-dimethylaminoethyl methacrylate, poly N,N-diethylaminoethyl methacrylate, poly N,N-dimethylaminopropyl acrylamide, and salts of these, etc.

The hydrogel polymer may also comprise poly(ethylene glycol) (PEG), (poly(propylene oxide) and/or poly(ethylene oxide).

The hydrogel polymer may also comprise a natural polymer. As used herein the term "natural polymer" refers to naturally occurring polymers as well as polymers consisting of natural building blocks. Thus natural polymers may for example be polypeptides or polysaccharides. The hydrogel may consist of said natural polymer or polymer consisting of natural building blocks, or the hydrogel may comprise both synthetic polymer(s) and natural polymers, which optionally may be covalently linked to each other. Said natural polymer may for example be a polypeptide that mimic collagenase substrates, it may be extracellular matrices, fibrinogen, HA, alginate or chitosan.

The process for combining the above block having a cloud point with the hydrophilic block is not particularly limited. For example, it is preferred to obtain a block copolymer, or a graft copolymer, or a dendrimer-type copolymer containing these blocks.

A 10 percent-aqueous solution of the above hydrogel polymer may preferably show a viscosity of 10-3,000 Pa*s (10-3,000 centipoises), more preferably, 50-1,000 Pa*s (50-1,000 centipoises) at 5 degrees C.

In order to reduce or prevent cytotoxicity, it is preferred to use a hydrogel-polymer which can be converted into a gel state at a concentration of 20 percent or less (more preferably 15 percent or less, particularly 10 percent or less), wherein the concentration is {(polymer)/(polymer+dispersion liquid)}.

The support may also comprise additional components, for example components beneficial for maintenance and/or growth of cells. Thus, in embodiments of the invention where the support is a hydrogel, then in addition to the dispersion liquid and the hydrogel polymer, the support may also comprise additional components.

Said additional components may for example be antibiotics, ECM such as collagen or gelatin, hormones such as insulin and growth factors, and other cells or tissues capable of secreting same, or fatty acid derivatives such as prostaglandins.

The support may also be a co-polymer, for example a co-polymer selected from the group consisting of pluronic lecithin organogels and alginate hydrogels.

The cell-compatible hydrogel to be used with the invention may for example be a gelatinous gel. Examples of gelatinous gels include Matrigel™ and Puragel™.

Examples of useful cell-compatible hydrogels to be used with the invention and methods for designing same are described by Seliktar, 2012, Science, 336:1124-1128.

Specific examples of useful hydrogels to be used with the present invention may be selected from the group consisting of h9e, Matrigel™, Puragel™, Pluronic, Puramatrix, and alginate hydrogel. Further examples of useful hydrogels are provided in Tables 1 and 2 of international patent application WO 2016/000721 (see p. 31 to 38 therein).

The standard handling of Matrigel is to keep it at low temperature (e.g. in the range of 0 to 8° C., for example at a temperature in the range of 0 to 5° C.) while adding cells. After the cells are embedded in the gel, the temperature is raised to in the range of 20° C. to 40° C., such as in the range of 22° C. to 37° C. and Matrigel will gel (enter gel-phase). The cells will now be allowed to grow in the 3D structure. Other hydrogels having a sol-gel transition temperature in the range of 10 to 35° C. may be handled in a similar manner.

Incubating in Cell-Compatible Support

As noted above, the methods of the invention may comprise a step of incubating the tissue fragments in a cell-compatible support. Said cell-compatible support may be any of the above-mentioned cell-compatible supports.

The methods also involve a step of incubating a random selection of said tumoroids with various test combinations under conditions supporting 3 dimensional maintenance and/or growth of human or other mammalian cells. Typically that comprises incubating the selection of tumoroids in a cell-compatible support, such as any of the above-mentioned cell-compatible supports. As described above said test combinations may be:

- a platinum compound
- a platinum compound and one or more additional anti-cancer compounds.

As mentioned above, individual selections of tumoroids are typically incubated separately with different test combinations in individual containers/wells/compartments. After incubation, each container/well/compartment is inspected as to whether growth/viability/metabolism of the tumoroids has been inhibited.

The platinum compounds and optionally additional anti-cancer compounds may be added to the tumoroids in any suitable manner. For example, the platinum compounds and optionally additional anti-cancer compounds may be mixed with the cell-compatible support prior to addition of the tumoroids, it may be added simultaneously with the tumoroids, or it may be added after the tumoroids have settled in the cell-compatible support.

In a preferred embodiment of the invention, the cell-compatible support is a sol-gel, which reversible can change between a sol-state and a gel-state. In that manner the test combinations as well as the tissue fragments or tumoroids may be mixed with the cell-compatible support, while said support is in the sol-state, where after the cell-compatible support may be brought to the gel-state thereby entrapping the cells in the gel.

In one embodiment, incubation of the tumoroids in a cell-compatible support comprises the steps of i. contacting separate cell-compatible supports with each test combination;

ii. contacting each cell-compatible support with a random selection of tumoroids, wherein said cell-compatible support is brought to the sol-state either before or during contact between the cell-compatible support and said tumoroids;

wherein steps i. and ii. may be performed simultaneously or sequentially in any order iii. bringing the cell-compatible support to the gel-state thereby entrapping tumoroids in the support; and iv. incubating the cell-compatible support in the gel-state under conditions supporting growth of human or other mammalian cells.

In another embodiment, incubation of the tumoroids in a cell-compatible support comprises the steps of i. providing a container comprising the cell-compatible support comprising the test composition in the gel state;

ii. contacting the cell-compatible support with the random selection of tumoroids;

iii. bringing the cell-compatible support to the sol-state;

iv. bringing the support to the gel-state thereby entrapping cells in the support; and v. incubating the cell-compatible support in the gel-state under conditions supporting growth of human or other mammalian cells.

In one embodiment, the tissue fragments or the random selection of tumoroids are added to the support (e.g. the hydrogel), while the support is in the gel-state (e.g. the hydrogel is in the gel-phase).

In one embodiment, the test combinations are added to the support (e.g. the hydrogel), while the support is in the gel-state (e.g. the hydrogel is in the gel-phase).

Preferably, the tissue fragments or the tumoroids are allowed to settle into the container/wells/compartments, and excess liquid may be removed. The sample may for example be contained in a transport buffer. The transport buffer may be any aqueous medium agreeable to cells, such as growth medium, STEM medium or a physiological saline, such as PBS. The tissue fragments may be allowed to settle into the container/wells/compartments by gravity, and the liquid of the cell suspension in the reservoir may be removed.

Once the tissue fragments or the tumoroids are in contact with the support, then the support may be brought to the sol-state. Depending on the nature of the support, the support may be brought into the sol-state by a number of methods. In embodiments of the invention, wherein the support is a sol-gel with a transition temperature, then this is accomplished by transferring to a temperature, wherein the sol-gel is in the sol-state. Typically, this is accomplished by transferring to a temperature below the transition temperature of said sol-gel.

Once the support is in the sol-state, the tissue fragments or tumoroids are allowed to flow into the support. This may be accomplished by gravity. When the cells are in a desired position the support is brought into the gel-state thereby entrapping the cells in the support. In particular, it is preferred that the tissue fragments or tumoroids are allowed to settle in a narrow field, which may facilitate monitoring the cells using an optical device like a microscope. Thus, preferably, the tissue fragments or tumoroids are allowed to settle in a field sufficiently narrow to allow inspection of the cells with a microscope or other equipment for imaging, wherein essentially all cells can be inspected without the need to change focus of said microscope. In a preferred embodiment of the invention, the tissue fragments or tumoroids are allowed to settle at the bottom of the well/compartment. Thus, at least 70%, such as at least 80%, for example at least 90%, such as essentially all of the cells of the sample are allowed to settle at the bottom of the well/compartment, where after the support is brought into the gel-state. If tissue fragments or tumoroids are allowed to settle at the bottom of the well/compartment, this may facilitate monitoring the cells using an optical device like a microscope.

Depending on the nature of the support, the support may be brought into the gel-state by a number of methods. In embodiments of the invention, wherein the support is a sol-gel with a transition temperature, then this is accomplished by transferring the array to a temperature, wherein the sol-gel is in the gel state. Typically, this is accomplished by transferring the array to a temperature above the transition temperature of said sol-gel. Said temperature is preferably also a temperature allowing maintenance and/or growth of cells. Thus, it is preferred that said temperature is in the range of 30 to 45° C., such as in the range of 35 to 38° C., for example around 37° C.

The support with the tissue fragments or tumoroids is then allowed to incubate for a time sufficient to monitor, whether the cells are growing. Typically, said sample or part thereof is incubated in said cell-compatible support for in the range of 3 to 90 days, for example for in the range of 3 to 21 days. For example, the incubation may be for in the range to 1 to 20 days, such as in the range of 2 to 10 days.

The incubation should be performed under conditions supporting growth of human or other mammalian cells. In general, such conditions comprise high humidity, preferably close to 100%, approximately 5% $CO_2$ and around 37° C.

In general the cell-compatible support comprises a hydrogel comprising a dispersion liquid, which is a cell cultivation medium. Thus, additional cell cultivation medium may not be required.

After incubation the container may be investigated for whether the cells have been growing as described below in the section "Inhibition of growth, viability and/or metabolism".

Inhibition of Growth

The invention relates to methods for predicting the efficacy and/or resistance to one or more treatments in individuals suffering from colon cancer. The methods comprises providing a colon cancer biopsy from the individual, generating tumoroids thereof, and testing whether growth and/or viability and/or metabolism of said tumoroids is inhibited by incubation with the compound(s) of said treatment. In particular, the method comprise testing whether growth is inhibited.

The invention surprisingly shows that inhibition of growth of tumoroids from a specific individual with platinum compounds, can be correlated to sensitivity of said compound in that specific individual. The finding is very surprising, because other studies have found that tumoroid activity prepared from cells of a given individual as determined by determining ATP levels could not be used to predict outcome for treatment with oxaliplatin (see Ooft et al., 2020). However, the present invention shows a correlation between inhibition of growth and in vivo sensitivity to platinum compounds.

In order to simplify this description the term "growth/viability/metabolism" is sometimes used in place of "growth and/or viability and/or metabolism". Both terms however have the same meaning.

Thus, after incubation of the tumoroids with the platinum compound and optionally additional anti-cancer compounds, it is determined whether growth/viability/metabolism of said tumoroids is inhibited. Preferably, it is determined whether growth is inhibited. In particular, the term "growth" as used herein in respect of tumoroids preferably refer to increase in size of the tumorids, i.e. an increase in volume, increase in the projected area and/or increase in weight of the tumoroids.

This may be done by comparing the growth/viability/metabolism of said tumoroids with the growth/viability/metabolism of control tumoroids. In particular, the growth or growth inhibition may be compared to the growth or growth inhibition of control tumoroids. The control tumoroids may be tumoroids prepared in the same manner from a colon cancer biopsy from the same individual, but cultivated in the absence of said platinum compound (and additional anti-cancer compounds). For example, once tumoroids have been generated from the tissue fragments of the colon cancer biopsies, said tumoroids may be distributed into different random selections of tumoroids, wherein one or more selections are incubated with platinum compound(s) and optionally additional anti-cancer compounds and at least one random selection is the control.

Alternatively, inhibition of growth/viability/metabolism may be determined by comparing the growth/viability/metabolism of said tumoroids with the growth/viability/metabolism of a panel of reference tumoroids, wherein the reference tumoroids are tumoroids prepared from colon cancer biopsies from other individual(s) cultivated in the presence of the same platinum compound (and additional anti-cancer compounds), wherein it is known whether said compound(s) inhibits growth of tumoroids from said individual(s). If the growth/viability/metabolism of the tumoroids is comparable to growth/viability/metabolism of the reference tumoroids, the growth/viability/metabolism is inhibited to the same extent as the compound(s) inhibits growth/viability/metabolism of the reference tumoroids.

Growth or inhibition of growth can be measured in many different ways. Growth can for example be determined by determining the volume of the tumoroids or the change in volume of the tumoroids within a given time period. Said volume may be the volume of live cells within said tumorids. Alternatively, growth or inhibition of growth can be determined by determining the projected area, e.g. the largest projected area of the tumoroids or the change in projected area (largest projected area) of the tumoroids within a predetermined time. The "projected area" is the two dimensional area measurement of a three-dimensional object by projecting its shape on to an arbitrary plane. In respect of the present invention, the projected area may for example be determined by taking a 2D picture of the tumoroid(s) and determining the area on said picture. The projected area may be determined from any random angle, however it is preferred that if the change in growth is determined, the projected area is determined from essentially the same angle over time. In some embodiments, the projected area is the largest projected area.

In some embodiments, the projected area may be the projected area (e.g. the largest project area) of live cells within said tumoroids. It is also possible to determine growth or inhibition of growth by determining the weight of the tumoroids or the change in weight of the tumoroids within a given time period. If more than one tumoroid is used, an average growth of the tumoroids may be used. Determination of weight of tumoroids may be done in any useful manner, for example as described by Cristaldi D A et al., 2020.

In one preferred embodiment, said volume or said projected area is determined or monitored using an optical imaging instrument. Imaging may be done in one or more different physical planes. For determination of volume, it is preferred that imaging is done in multiple physical plans. For determination of projected area it may be sufficient to do imaging in one physical plan, but imaging may be performed in multiple physical plans. Determining or monitoring size of tumoroids using an optical imaging instrument is also referred to as "imaging" herein. Said optical imaging instrument may for example be optical brightfield and/or fluorescence microscopes, optical scanning devices, confocal microscopes, or optical coherence tomography. The optical imaging instrument may also combine two or more of the aforementioned. In a preferred embodiment, the optical imaging instrument is a combined optical brightfield and fluorescence microscope, Before imaging, the tumoroids may optionally be stained, with any useful staining. For example, live cells within the tumoroids may be stained by any stain marking live cells. Non-limiting examples of useful stainings include CyQUANT, or other cell viability/proliferation probes from Thermo Fisher Scientific as described in "Overview of Probes for Cell Viability, Cell Proliferation and Live-Cell Function-Section 15.1| Thermo Fisher Scientific—DK" or the probes described in The Molecular Probes Handbook (Wiederschain, G. Y). The imaging may be performed manually or in an automated way. A non-limiting useful imaging method, which can be used with the methods of the invention is described in Example 2. The skilled person understands that the imaging method described in Example 2 can be applied to determine growth or inhibition of growth of any tumoroids.

In general, if the growth of the tumoroids is reduced by at least 10% after incubation with a given platinum compound and optionally one or more additional anti-cancer compounds compared to the growth of control tumoroids, the growth is considered to be inhibited.

In preferred embodiments, the relative growth inhibition is determined. The relative growth inhibition is preferably determined by a method comprising the steps of Determining the relative growth of test tumoroids, wherein the test tumoroids are incubated with the platinum compounds (and optionally additional anti-cancer compounds) by determining the size of the test tumoroids before and after said incubation, and dividing the size after said incubation with the size before incubation Determining the relative growth of control tumoroids by determining the size of said control tumoroids, incubating the control tumoroids for the same amount of time and under the same conditions as the test tumoroids except that the control tumoroids are incubated in the absence of said platinum compounds (and optionally additional anti-cancer compounds) and dividing the size after said incubation with the size before incubation Determining the relative growth inhibition by dividing the relative growth of the test tumoroids with the relative growth of the control tumoroids.

The relative growth inhibition will in general be a number in the range of 0 to 1, unless the test tumoroids grow better than the control tumoroids, which will rarely be the case.

The control tumoroids may in particular be tumoroids prepared in the same manner as the test tumoroids from a colon cancer biopsy from the same individual, but cultivated in the absence of said platinum compound (and additional anti-cancer compounds) as described above.

A low relative growth inhibition indicates high sensitivity to the particular platinum compound (and additional anti-cancer compounds). Conversely, a relative growth inhibition close to 1 means that the particular platinum compound (and additional anti-cancer compounds) was completely unable to inhibit tumoroid growth.

In general, if the relative growth inhibition of the tumoroids is lower than 0.9, the growth is considered to be inhibited. In some embodiments, if the relative growth inhibition of the tumoroids is lower than 0.8, for example lower than 0.7 the growth is considered to be inhibited.

Viability may for example be determined by determining the number of viable cells of the tumoroids, by determining the percentage of viable cells of the tumoroids compared to the total number of cells or by determining the change in the number or percentage of viable cells within a given time period. The skilled person is aware of various methods for determining the number or the percentage of viable cells. This may for example be determined taking advantage of any of the commercially available live/dead kits, which can be used to discriminate living from dead cells, e.g. the fluorescence-based Invitrogen LIVE/DEAD assay.

In general, if the number or the percentage of viable cells or the change thereof is reduced by at least 10% after incubation with a given platinum compound and optionally one or more additional anti-cancer compounds compared to the number or percentage of viable cells or change thereof of control tumoroids, viability is considered to be inhibited.

Metabolism may be determined in a number of different ways. Metabolism may for example be determined by determining the level or change in level of one or more compounds indicative of metabolic activity, for example ATP.

Alternatively, metabolic activity may be determined by determining the potential over the mitochondric membranes.

In general, if the level or change in level of said one or more compounds indicative of metabolic activity (e.g. ATP) is reduced by at least 10% after incubation with a given platinum compound and optionally one or more additional anti-cancer compounds compared to the level or change in level of said one or more compounds in control tumoroids, metabolism is considered to be inhibited.

As described herein elsewhere, metabolism of tumoroids is not as sensitive a method as determination of growth. Thus, determination of inhibition of metabolism in tumoroids prepared from cells of a given individual, does not necessarily correlate with in vivo effect in said individual. It is therefore preferred that the methods of the invention involve determination of growth or inhibition of growth.

Items

The invention may further be defined by the following items.

1. A method for predicting the efficacy of treatment of colon cancer with one or more different treatments in an individual suffering from said cancer, wherein each treatment is treatment with a platinum compound and optionally one or more additional anti-cancer compounds, said method comprising the steps of
   a) providing at least one colon cancer biopsy obtained from said individual,
   b) dissociating the biopsy into tissue fragments each comprising a plurality of cells attached to each other,
   c) incubating said tissue fragments in a cell-compatible support, which supports 3 dimensional maintenance and/or growth of human cells to generate tumoroids,
   d) incubating a random selection of said tumoroids with the platinum compound (and additional anti-cancer compound(s)) of each treatment under conditions supporting 3 dimensional maintenance and/or growth of human cells
   e) determining whether growth/viability/metabolism of said tumoroids is inhibited by incubation with said platinum compound (and additional anti-cancer compound(s)), wherein inhibition of growth/viability/metabolism of said tumoroids by a platinum compound (and additional anti-cancer compounds) of a given treatment is indicative of efficacy of said treatment of colon cancer in said individual.
2. A method for predicting resistance to treatment with one or more different treatments of colon cancer in an individual suffering from said cancer, wherein each treatment is treatment with a platinum compound and optionally one or more additional anti-cancer compounds, said method comprising the steps of
   a) providing at least one colon cancer biopsy obtained from said individual,
   b) dissociating the biopsy into tissue fragments each comprising a plurality of cells attached to each other,
   c) incubating said tissue fragments in a cell-compatible support, which supports 3 dimensional maintenance and/or growth of human cells to generate tumoroids,
   d) incubating a random selection of said tumoroids with the platinum compound (and additional anti-cancer compound(s)) of each treatment under conditions supporting 3 dimensional maintenance and/or growth of human cells
   e) determining whether growth/viability/metabolism of said tumoroids is inhibited by incubation with said platinum compound (and additional anti-cancer compound(s)), wherein inhibition of growth/viability/metabolism of said tumoroids by a platinum compound (and additional anti-cancer compounds) of a given treatment is indicative of said colon cancer in said individual not being resistant to said treatment.
3. A method of identifying a platinum compound, which alone or in combination with one or more additional anti-cancer compounds are likely to be efficient in treatment of colon cancer in an individual in need thereof, said method comprising the steps of
   a) providing at least one colon cancer biopsy obtained from said individual,
   b) dissociating the biopsy into tissue fragments each comprising a plurality of cells attached to each other,
   c) incubating said tissue fragments in a cell-compatible support, which supports 3 dimensional maintenance and/or growth of human cells to generate tumoroids,
   d) providing a plurality of test combinations, wherein each test combination comprises a platinum compound and optionally one or more additional compounds
   e) incubating individual random selections of said tumoroids with each of the test combinations under conditions supporting 3 dimensional maintenance and/or growth of human cells
   f) determining whether growth/viability/metabolism of said tumoroids is inhibited by incubation with said test combinations, wherein inhibition of growth/viability/metabolism of said tumoroids by a given test combination is indicative of efficacy of treatment of colon cancer in said individual with the platinum compound (and additional anti-cancer compounds) of said test combination.
4. A method for predicting the efficacy of treatment of colon cancer with one or more different treatments in an individual suffering from said cancer, wherein each treatment is treatment with a platinum compound and optionally one or more additional anti-cancer compounds, said method comprising the steps of
   a) providing at least one colon cancer biopsy obtained from said individual,
   b) dissociating the biopsy into single cells or tissue fragments comprising a plurality of cells attached to each other,
   c) incubating said cells or tissue fragments in a cell-compatible support, which supports 3 dimensional maintenance and/or growth of human or other mammalian cells to generate tumoroids,
   d) incubating a random selection of said tumoroids with the platinum compound (and additional anti-cancer compound(s)) of each treatment under conditions supporting 3 dimensional maintenance and/or growth of human or other mammalian cells
   e) determining whether growth of said tumoroids is inhibited by incubation with said platinum compound (and additional anti-cancer compound(s)), wherein inhibition of growth of said tumoroids by a platinum compound (and additional anti-cancer compounds) of a given treatment is indicative of efficacy of said treatment of colon cancer in said individual.

5. A method for predicting resistance to treatment with one or more different treatments of colon cancer in an individual suffering from said cancer, wherein each treatment is treatment with a platinum compound and optionally one or more additional anti-cancer compounds, said method comprising the steps of
   a) providing at least one colon cancer biopsy obtained from said individual,
   b) dissociating the biopsy into single cells or tissue fragments comprising a plurality of cells attached to each other,
   c) incubating said cells or tissue fragments in a cell-compatible support, which supports 3 dimensional maintenance and/or growth of human or other mammalian cells to generate tumoroids,
   d) incubating a random selection of said tumoroids with the platinum compound (and additional anti-cancer compound(s)) of each treatment under conditions supporting 3 dimensional maintenance and/or growth of human or other mammalian cells
   e) determining whether growth of said tumoroids is inhibited by incubation with said platinum compound (and additional anti-cancer compound(s)),
   wherein inhibition of growth of said tumoroids by a platinum compound (and additional anti-cancer compounds) of a given treatment is indicative of said colon cancer in said individual not being resistant to said treatment.
6. A method of identifying a platinum compound, which alone or in combination with one or more additional anti-cancer compounds are likely to be efficient in treatment of colon cancer in an individual in need thereof, said method comprising the steps of
   a) providing at least one colon cancer biopsy obtained from said individual,
   b) dissociating the biopsy into single cells or tissue fragments comprising a plurality of cells attached to each other,
   c) incubating said cells or tissue fragments in a cell-compatible support, which supports 3 dimensional maintenance and/or growth of human or other mammalian cells to generate tumoroids,
   d) providing a plurality of test combinations, wherein each test combination comprises a platinum compound and optionally one or more additional compounds
   e) incubating individual random selections of said tumoroids with each of the test combinations under conditions supporting 3 dimensional maintenance and/or growth of human or other mammalian cells
   f) determining whether growth of said tumoroids is inhibited by incubation with said test combinations,
   wherein inhibition of growth of said tumoroids by a given test combination is indicative of efficacy of treatment of colon cancer in said individual with the platinum compound (and additional anti-cancer compounds) of said test combination.
7. The method according to any one of the preceding items, wherein said cancer is metastatic colon cancer.
8. The method according to item 7, wherein the biopsy is from a metastasis.
9. The method according to any one of the preceding items, wherein at least one platinum compound is selected from the group consisting of carboplatin, cisplatin, cisplatinum, oxaliplatin and satraplatin.
10. The method according to any one of the preceding items, wherein the platinum compound is oxaliplatin.
11. The method according to any one of the preceding items, wherein said tumoroids are incubated with in the range of 0.4 to 20 μM, such as in the range of 0.4 to 10 μM of said platinum compound.
12. The method according to any one of the preceding items, wherein at least one additional anti-cancer compound is a fluoropyrimidine, for example a fluoropyrimidine selected from the group consisting of 5-fluorouracil (5-FU), capecitabine and tegafur.
13. The method according to any one of the preceding items, wherein at least one additional anti-cancer compound is a taxane, for example a taxane selected from the group consisting of taxol and docetaxel.
14. The method according to any one of the preceding items, wherein at least one additional anti-cancer compound is a PARP inhibitor, for example a PARP inhibitor selected from the group consisting of olaparib, rucaparib, niraparib, talazoparib, veliparib and pamiparib.
15. The method according to any one of the preceding items, wherein at least one additional anti-cancer compound is an immune checkpoint inhibitor, for example an immune checkpoint inhibitor selected from the group consisting of inhibitors of CTLA4, PD-1 and PD-L1.
16. The method according to any one of the preceding items, wherein at least one additional anti-cancer compound is an antibody, for example an antibody selected from the group consisting of cetuximab, bevacizumab, panitumumab, ramucirumab and necitumumab.
17. The method according to any one of the preceding items, wherein said additional anti-cancer compounds are not SN38.
18. The method according to any one of the preceding items, wherein one of the treatments is treatment with a combination of 5-FU, oxaliplatin and folinic acid or one of the test combinations is a combination of 5-FU, oxaliplatin and folinic acid.
19. The method according to item 18, wherein said tumoroids are incubated with said combination at a concentration of
   a) in the range of 0.1 to 20 μM, for example in the range of 1 to 20 μM, such as in the range of 5 to 10 μM 5-FU,
   b) in the range of 0.4 to 20 μM, such as in the range of 0.4 to 10 μM, for example in the range of 2 to 7 μM oxaliplatin and/or
   c) in the range of 0.1 to 20 μM, for example in the range of 1 to 20 μM, such as in the range of 5 to 10 μM folinic acid.
20. The method according to any one of the preceding items, wherein one of the treatments is treatment with a combination of 5-FU, oxaliplatin, SN-38 and folinic acid or one of the test combinations is a combination of 5-FU, oxaliplatin, SN-38 and folinic acid.
21. The method according to item 20, wherein said tumoroids are incubated with said combination at a concentration of
   a) in the range of 0.1 to 20 μM, such as in the range of 0.5 to 5 μM 5-FU,
   b) in the range of 0.4 to 20 μM, such as in the range of 0.4 to 10 μM, for example in the range of 0.4 to 1 μM oxaliplating and/or
   c) in the range of 0.1 to 20 μM, such as in the range of 0.5 to 5 μM folinic acid.

22. The method according to any one of the preceding items, wherein said biopsy is dissociated into tissue fragments each comprising a plurality of cells attached to each other.
23. The method according to any one of the preceding items, wherein the tissue fragments have a diameter of at least 30 μm.
24. The method according to any one of the preceding items, wherein the tissue fragments have a diameter of at least 50 μm, for example at least 70 μm.
25. The method according to any one of the preceding items, wherein the tissue fragments have a diameter of at the most 100 μm.
26. The method according to any one of the preceding items, wherein the tissue fragments have a diameter in the range of 70 to 100 μm.
27. The method according to any one of the preceding items, wherein the majority of the tissue fragments comprises at least 10 cells attached to each other, such as in the range of 10 to 50 cells attached to each other.
28. The method according to any one of the preceding items, wherein at least 90% of the tissue fragments comprises at least 10 cells attached to each other, such as in the range of 10 to 50 cells attached to each other.
29. The method according to any one of the preceding items, wherein a proteolytic enzyme specifically cleaving peptide bonds on the C-terminal side of lysine and arginine is not added to said tissue fragments or to said tumoroids at any time during the procedure.
30. The method according to any one of the preceding items, wherein the method does not contain a step of dissociating the tissue fragments into single cells.
31. The method according to any one of the preceding items, wherein the method does not contain a step of dissociating the tumoroids into single cells.
32. The method according to any one of the preceding items, wherein the method does not contain a step of dissociating the tumoroids obtained in step c) into smaller fragments.
33. The method according to any one of the preceding items, wherein the cell-compatible support is a sol-gel, which reversible can change between a sol-state and a gel-state.
34. The method according to item 33, wherein said support is a temperature reversible gel.
35. The method according to any one of the preceding items, wherein the step of incubating said tumoroids with the platinum compound or the test combination comprises the steps of
   i. contacting separate cell-compatible supports with the platinum compound (and additional anti-cancer compound(s)) of each treatment or with each test combination;
   ii. contacting each cell-compatible support with a random selection of tumoroids, wherein said cell-compatible support is brought to the sol-state either before or during contact between the cell-compatible support and said tumoroids;
   wherein steps i. and ii. may be performed simultaneously or sequentially in any order,
   iii. bringing the cell-compatible support to the gel-state thereby entrapping tumoroids in the support; and
   iv. incubating the cell-compatible support in the gel-state under conditions supporting growth of human cells.
36. The method according to any one of the preceding items, wherein the step of incubating said tumoroids with the platinum compound or the test combination comprises the steps of
   i. Providing separate containers comprising the cell-compatible support comprising the platinum compound (and additional anti-cancer compound(s)) of each treatment or with each test combination in the gel state;
   ii. contacting the cell-compatible support with a random selection of tumoroids;
   iii. bringing the cell-compatible support to the sol-state;
   iv. bringing the support to the gel-state thereby entrapping cells in the support; and
   v. incubating the cell-compatible support in the gel-state under conditions supporting growth of human cells.
37. The method according to any one of the preceding items, wherein inhibition of growth is determined by determining the volume of the tumoroids or the change in volume of the tumoroids.
38. The method according to any one of the preceding items, wherein inhibition of growth is determined by determining the projected area of the tumoroids or the change in the projected area of the tumoroids.
39. The method according to any one of the preceding items, wherein inhibition of growth is determined by determining the largest projected area of the tumoroids or the change in the largest projected area of the tumoroids.
40. The method according to any one of items 37 to 39, wherein said volume is the volume of live cells within said tumoroids and/or said area is the projected area or the largest projected area of live cells within said tumoroids.
41. The method according to any one of the preceding items, wherein inhibition of growth is determined by determining the volume, the projected area or the largest projected area of the tumoroids or the change in volume, projected area or largest projected area of the tumoroids by imaging.
42. The method according to any one of the preceding items, wherein inhibition of growth is determined by determining the weight of the tumoroids or the change in weight of the tumoroids.
43. The method according to any one of the preceding items, wherein inhibition of growth/viability/metabolism of said tumoroids by at least 10% is indicative of efficacy or no resistance.
44. The method according to any one of the preceding items, wherein the step of determining whether growth of the tumoroids is inhibited does not comprise a step of measuring ATP.
45. The method according to any one of the preceding items, wherein inhibition of growth is determined by determining the relative growth inhibition, wherein the relative growth inhibition is determined by a method comprising the steps of
a) determining the relative growth of tumoroids incubated with the platinum compounds (and optionally additional anti-cancer compounds) by determining the size of the tumoroids before and after said incubation, and dividing the size after said incubation with the size before incubation, wherein said tumroids are referred to as “test tumoroids”; and
b) determining the relative growth of control tumoroids by determining the size of said control tumoroids, incubating the control tumoroids for the same amount of time and under the same conditions as the test tumoroids except that the control tumoroids are incubated in the absence of said platinum compounds (and optionally additional anti-cancer compounds) and dividing the size after said incubation with the size before incubation; and c) determining the relative growth inhibition by dividing the relative growth of the test tumoroids with the relative growth of the control tumoroids wherein a low relative growth inhibition is indicative of high inhibition of growth.

46. The method according to item 45, wherein a relative growth inhibition of less than 0.9 is considered inhibition of growth.

47. A method of treatment of an individual suffering from colon cancer, said method comprising the steps of a) identifying a platinum compound, which alone or in combination with one or more additional anti-cancer compounds is likely to be efficient in treatment of colon cancer in said individual by the method according to any one of items 3 to 0 b) administering said identified platinum compound or combination of platinum compound with one or more additional anti-cancer compounds to said individual thereby treating said colon cancer.

EXAMPLES

The invention is further illustrated by the following examples, which however should not be construed as limiting for the invention.

Example 1

Patients 45 adult patients were included. To be enrolled in the trial patients had to have progressive non-resectable metastatic colon cancer and been exposed to various available therapies including fluoropyrimidine-, oxaliplatin- and irinotecan-based chemotherapies, anti-VEGF agents and/or anti-EGFR agents if RAS/RAF wild-type. These patients were thus clinically drug resistant (CDR) to the commonly used treatment regimens for colon cancer, Folfox, Folfiri and Folfoxiri, and thus corresponded to the population eligible for rescue treatment.

Biopsies from the colon cancers were obtained from the patients and tumoroids were cultivated from tissue fragments of the said biopsies as described in Example 2. Random selections of tumoroids thus obtained are separately cultivated in the presence of different anti-cancer compounds or combinations thereof essentially as described in Example 2 in order to identify the most effective in each patient.

The patients are treated with the identified anti-cancer compounds or combination of anti-cancer compounds. The patients are followed with resistance as the primary endpoint.

Example 2

Patients

The present analysis involves a subset of 19 of the CDR patients described in Example 1. The patients are third line CDR patients known to be resistant to oxaliplatin- and irinotecan-based regimens. The CDR patients were compared to a group of 8 colon cancer control patients, who had not had chemotherapy prior to tissue sampling, and thus likely are not resistant to the oxaliplatin- and irinotecan-based regimens. The main inclusion criterion for the CDR patients was that patients had progressed on oxaliplatin and irinotecan-based therapy such as Folfox, Folfiri and eventually Folfoxiri and therefore were categorised as clinically resistant to said regimes. The objective was to study if the methods of the invention could distinguish between CDR resistant patients and chemo-naive control patients for the regimens Folfox, Folfiri and Folfoxiri.

In CDR patient biopsies were sampled from metastases. In chemo-naive patient samples were collected from the primary tumor or resected liver metastases of 8 patients with colorectal cancer.

The study protocols were approved by the Regional Committee on Health Research Ethics-Capital Region of Denmark (protocol no. H-1-2011-125 and the Regional Committees on Health Research Ethics for Southern Denmark (protocol no. S20170028). Informed consent was obtained from all patients.

3D Tumoroid Preparation

For CDR patients, one to three 16-gauge ultrasonography- or CT-guided tumor biopsies were sampled from liver metastases. The biopsies were placed in Stem cell media (StemPro hESC SFM, Thermo Fisher Scientific, Waltham, MA, USA) supplemented with antibiotics (200 U/ml penicillin, 200 μg/ml streptomycin, 100 μg/ml gentamicin and 2.5 μg/ml amphotericin B) and transferred to the laboratory. The biopsies were minced into 1-2 mm pieces with a scalpel. Tissue pieces were seeded in 1:1 mix of stem cell media and Matrigel (BD Biosciences, Franklin Lakes, NJ, USA) in droplets of 50-80 ul in wells of a 24 well plate. The plate was incubated at 37° C. for 15-30 min followed by adding 850 ul Stem cell medium to each well. The tissue was cultured 3-7 days at 37° C. in a 5% $CO_2$ humidified incubator until tumoroids have formed.

Tumoroids were released from the tissue residue and Matrigel using a 1 ml pipette. The resulting tissue suspension was filtered sequentially through the following filters: 100 μm cell strainer, 70 μm cell strainer, 40 μm cell strainer and 30 μm cell strainer (all from BD Biosciences, Franklin Lakes, NJ, USA). Tissue fragments retained by the 100 μm filter was further mechanically disrupted using PBS with 0.1% BSA and filtered until no more tissue was left or until no more tumoroids could be extracted. The run through from the 100 μm strainer was applied to a 70 μm strainer and the run through from this filter was applied to the 40 μm strainer and so forth. The retained tumoroids in all the filters were secured by washing them out in Stem cell medium. Tumoroid suspensions were centrifuged at 250G for 5 min. Pellet (tumoroids) was resuspended in 50-200 ul Stem cell media followed by mixing it with equal volume of Matrigel. The tumoroid suspension was seeded in 50-80 ul droplets in a 24 well plate and cultured as described above.

The tumoroids were cultured for 4-7 days at 37° C. in a 5% $CO_2$ humidified incubator. Propagation was continued until enough tumoroids for sensitivity testing was achieved. Hereafter tumoroids were released from the Matrigel and prepared for screening by filtering them through a 100 um and 70 um strainer thus making a tumoroid suspension of 70-100 um. Tumoroids were added to the screening array pre-loaded with test compounds/compound combinations. At day 6 to day 7 tumoroids were stained with CyQUANT (cell proliferation assay). Tumoroid growth was measured by taking brightfield images on day 0 and visualizing living cells using CyQUANT Cell proliferation assay (ThermoFisher) on day 7. All images were acquired using a Cytation 1 (BioTek) imaging system.

For Control patients, tissue from resected tumor was used. This sampling method typically secures bigger amounts of tissue and mechanically as well as enzymatically digestion is performed.

Tumor tissue was washed in PBS with antibiotics, visible fatty and necrotic areas were removed with a scalpel. The tissue was minced into 1-2 mm pieces with a scalpel followed by digesting it with 1 mg/ml collagenase type II (Gibco, Thermo Fisher Scientific, Waltham, MA, USA) in PBS with antibiotics for 20 min at 37° C. The tissue fragment suspension was filtered sequentially through the following filters: 100 μm cell strainer (BD Biosciences, Franklin Lakes, NJ, USA), 40 μm cell strainer (BD Biosciences, Franklin Lakes, NJ, USA),) and 30 μm pre-separation filter (MACS, Miltenyi Biotec, Bergisch Gladbach, Germany). Tissue fragments retained by the 100 um strainer was collected and redigested for 10 min at 37° C. and passed through the filters again. This step was repeated until all tissue passed through the 100 μm filter. Retained tissue fragments were collected from the 100 μm, 40 μm and 30 μm filters, The isolated tissue fragments were seeded in stem cell medium (StemPro hESC SFM, Thermo Fisher Scientific, Waltham, MA, USA) supplemented with antibiotics (200 U/ml penicillin, 200 μg/ml streptomycin, 100 μg/ml gentamicin and 2.5 μg/ml amphotericin B) in petri dishes coated with agarose (Sigma-Aldrich, St. Louis, MO, USA) and cultured at 37° C. in a 5% $CO_2$ humidified incubator After 3 days of culture, tumoroids were washed in PBS, filtered, and resuspended in fresh stem cell medium. Tumoroids were mixed 1:1 with Matrigel (BD Biosciences, Franklin Lakes, NJ, USA) and seeded in 24-well plates in 50-80 um droplets topped with 850 ul stem cell media after polymerization of the Matrigel. The tumoroids were cultured for 4-7 days at 37° C. in a 5% $CO_2$ humidified incubator. Propagation was continued until enough tumoroids for sensitivity testing was achieved. Hereafter tumoroids were released from the Matrigel and prepared for screening by filtering them through a 100 um and 70 um strainer thus making a tumoroid suspension of 70-100 um tumoroids.

Tumoroids were added to the screening array pre-loaded with test compounds/compound combinations. At day 6 to day 7 tumoroids were stained with CyQUANT (cell proliferation assay). Tumoroid growth was measured by taking brightfield images on day 0 and visualizing living cells using CyQUANT Cell proliferation assay (ThermoFisher) on day 7. All images were acquired using a Cytation 1 (BioTek) imaging system.

$ED_{50}$

The test described herein measures the sensitivity of tumoroids from a given patient towards one or more test compounds or combinations thereof by comparing to growth of tumoroids from a panel of reference patients. The test compounds are usually anti-cancer compounds.

Each treatment regimen is treatment with one or a combination of anti-cancer compounds. The test is usually performed using a single contraction of the test compound(s). The single concentration is determined by first screening tumoroids obtained from several patients (typically 5-10) against a titration of the test compound(s) against 5 to 8 concentrations. For each patient and compound in the titration test the effective dose 50% ($ED_{50}$) is calculated by calculating the concentration of compound(s) that results in 50% inhibition of tumoroid growth when compared to the untreated control. The average $ED_{50}$ concentration is chosen for future sensitivity test.

The treatment regimen Folfox involves administration of 5-FU, oxaliplatin and folinic acid. The average $ED_{50}$ of a combination of these anti-cancer compounds was determined as described above to be 7 μM 5-FU, 4.2 μM oxaliplatin and 7 μM folinic acid.

The treatment regimen Folfiri involves administration of 5-FU, irinotecan and folinic acid. SN38 is the active metabolite of irinotecan and may be used for the test in place of irinotecan. The average $ED_{50}$ of these anti-cancer compounds was determined as described above to be 1.5 μM 5-FU, 12 nM SN38 and 1.5 μM folinic acid.

The treatment regimen Folfoxiri involves administration of 5-FU, oxaliplatin, irinotecan and folinic acid. The average $ED_{50}$ for a combination of these anti-cancer compounds was determined as described above to be 1 μM 5-FU, 0.6 μM oxaliplatin, 8 nM SN38 and 1 μM folinic acid.

Next, tumoroids from several patients (typically >9 patients) are tested for their sensitivity towards the average $ED_{50}$ concentration and these results serves as a "reference panel" to which future screens are compared. Thus, the test measures whether tumoroids of a given patient are equally-, more- or less sensitive to a test compound or combination of test compounds compared to other patients with the same cancer.

Test of Sensitivity

For each patient, the tumoroids established as described above were analysed for sensitivity towards different panels of drugs including Folfox (5-FU, 7 uM; Oxaliplatin, 4.2 uM; folinic acid, 7 uM), Folfiri (5-FU, 1.5 uM; SN38, 12 nM; folinic acid, 1.5 uM) and Folfoxiri (5-FU, 1 uM; Oxaliplatin, 0.6 uM; SN38, 8 nM; folinic acid, 1 uM). The tumoroids were grown in the presence of the drugs for 6 days and growth was compared to untreated tumoroids (negative controls). Tumoroid growth was measured by taking brightfield images on day 0 and visualizing living cells using CyQUANT Cell proliferation assay (ThermoFisher) on day 7. All images were acquired using a Cytation 1 (BioTek) imaging system.

Images from day 0 and day 7 were analysed using the Al image analysis algorithm IndiNet™, which quantifies the projected area (referred to as "area" in this example) of live cells in both brightfield (day 0) and fluorescence (day 7) images and calculates the relative growth inhibition. The relative growth inhibition is the relative growth (live cell area on day 7 divided by the live cell area on day 0) of drug treated tumoroids divided by the mean relative growth of negative controls. Thus, a high growth inhibition value indicates high sensitivity to the regiment. Conversely, a growth inhibition of 0% means that the regiment was completely unable to inhibit tumoroid growth.

Statistics Comparison of growth inhibition for each drug regimen was performed using a MannWhitney test in GraphPad Prism 8.4.3 (GraphPad Software LLC) with a confidence level of 95%. p-values below 0.05 were considered significant. K-means clustering was performed using the k-means function in Matlab 2018a (Mathworks).

Results

Tumoroids from nineteen CDR patients and eight chemonaive control patients were prepared, exposed to the standard chemotherapy regimens Folfox, Folfiri and Folfoxiri as described above and inhibition of tumoroid growth was calculated as described. In two CDR patients the generated tumoroid numbers were insufficient to test more than one of the regimens. One of the CDR patients did not pass quality control requirements for Folfox and Folfoxiri and these results were not included. All chemonaive patients were successful tested against all three regimens. For all three regimens, the IndiTreat® test showed that the growth inhibition of tumoroids from CDR patients was significantly less compared to chemonaive patients (FIG. 1). For each of the regimens tested the results for CDR patients and chemonaive patients were pooled and k-means clustering algorithm was used to generate a blind clustering of the results into two groups. For the CDR patients the clustering showed that the test identified between 81%-94% of the patients as having a low growth inhibition (Folfiri 94%, Folfox 81% and Folfoxiri 82%) Conversely, for chemonaive patients the test identified between 88%-100% of the patients having high growth inhibition (Folfiri 88%, Folfox 100% and Folfoxiri 100%). Low growth inhibition is typically inhibition of less than 10%, whereas inhibition of more than 10% is high growth inhibition.

Discussion

International guidelines for first line treatment of metastatic colorectal cancer include chemotherapy with Folfox, Folfiri or in selected patients Folfiri regimens with the addition of cetuximab or panitumumab in KRASwt patients. The response rate in first line therapy is 56% for Folfiri and 54% for Folfox. In second line the corresponding rates drop to 4% and 15%, respectively. Therefore, it is of great importance to begin treatment with the most effective chemotherapy regimen.

To date, there are no established biomarkers able to predict the response rate at the individual patient level to these chemotherapy regimens. The data presented here show that the 3D-tumoroid based test system IndiTreat® with a high degree of precision is able to identify patients that are clinically resistant to the regimens of Folfox, Folfiri and Folfoxiri.

This finding is surprising in light of other recent prospective studies showing that another test using 3D organoid cultures from chemonaive patients could predict sensitivity to Folfiri, whereas the test failed to identify Folfox-resistant patients (Ooft et al, 2020).

Different culture and assay conditions likely explain the different outcome. The two test systems thus differ in the procedures used to establish the 3D cultures. The IndiTreat system uses fragments of the patient's tumor (Jeppesen et al., 2017) whereas the procedure used by Ooft et al., 2020 is based separating the tumor tissue to single cells and allowing them to grow into organoids. Furthermore, the procedure used by Ooft et al., 2020 measures ATP in the tumoroids rather than inhibition of growth.

Example 3

Comparison between imaging of tumoroid growth and level of ATP release

Drug Sensitivity Measured with Imaging

The tumoroids were prepared from patient samples as described above in Example 2 under "3D tumoroid preparation". The tumoroids were added to drug screening arrays that we pre-loaded with varying concentrations of Oxaliplatin (3, 10, 30, 100, 300 uM), FOLFOX (0, 1, 0, 3, 1, 3, 10 30 uM. Equal concentrations of 5-Fluorouracil and Oxaliplatin) and SN38 (10, 30, 100, 300, 1000 nM). SN38 is the active components of Irinotecan. At day 6 to day 7 tumoroids were stained with CyQUANT (cell proliferation assay). Tumoroid growth was measured by taking brightfield images on day 0 and visualizing living cells using CyQUANT Cell proliferation assay (ThermoFisher) on day 7. All images were acquired using a Cytation 1 (BioTek) imaging system. For Control patients, tissue from resected tumor was used. This sampling method typically secures bigger amounts of tissue and mechanically as well as enzymatically digestion is performed.

Images from day 0 and day 7 were analysed using the AI image analysis algorithm IndiNet™, which quantifies the projected area (referred to as "area" in this example) of live cells in both brightfield (day 0) and fluorescence (day 7) images and calculates the relative growth inhibition. The relative growth inhibition is the relative growth (live cell area on day 7 divided by the live cell area on day 0) of drug treated tumoroids divided by the mean relative growth of negative controls. Thus, a low relative growth inhibition value indicates high sensitivity to the regiment. Conversely, a relative growth inhibition close to 1 means that the regiment was completely unable to inhibit tumoroid growth.

Drug Sensitivity Measured with Measurement of ATP Content

The tumoroids were prepared from the same patient samples as described above under "drug sensitivity measured with imaging". The tumoroids were added to drug screening arrays that we pre-loaded with varying concentrations of Oxaliplatin (3, 10, 30, 100, 300 uM), FOLFOX (0, 1, 0, 3, 1, 3, 10 30 uM. Equal concentrations of 5-Fluorouracil and Oxaliplatin) and SN38 (10, 30, 100, 300, 1000 nM). ATP content of cells in the tumoroids was measured day 0 and on day 7 using CellTiter-Glo 3D cell viability assay (Promega; Catalog number G9681). The homogenous CellTiter-Glo 3D assays generates a luminescent signal that is proportional to the amount of cellular ATP. The assay was conducted in accordance with the instructions from the manufacture (Promega) by allowing the drug screening arrays to equilibrate to room temperature (20-25° C.) and then adding an amount of the CellTiter-Glo 3D reagent to the drug screening arrays. The equal volume of media and reagent is mixed thoroughly for 5 min to induce cell lysis and release of cellular ATP content. The luminescence signal was monitored with the Cytation 1 (BioTek) imaging system operating in luminescence mode. The luminescence signal was quantified by direct comparison to an ATP dose-response curve created by replacing the drug screening media with ATP standards.

Statistics

Comparison of growth inhibition for each drug regimen was performed using a MannWhitney test in GraphPad Prism 8.4.3 (GraphPad Software LLC) with a confidence level of 95%. p-values below 0.05 were considered significant. K-means clustering was performed using the k-means function in Matlab 2018a (Mathworks).

Results

Figure 2:
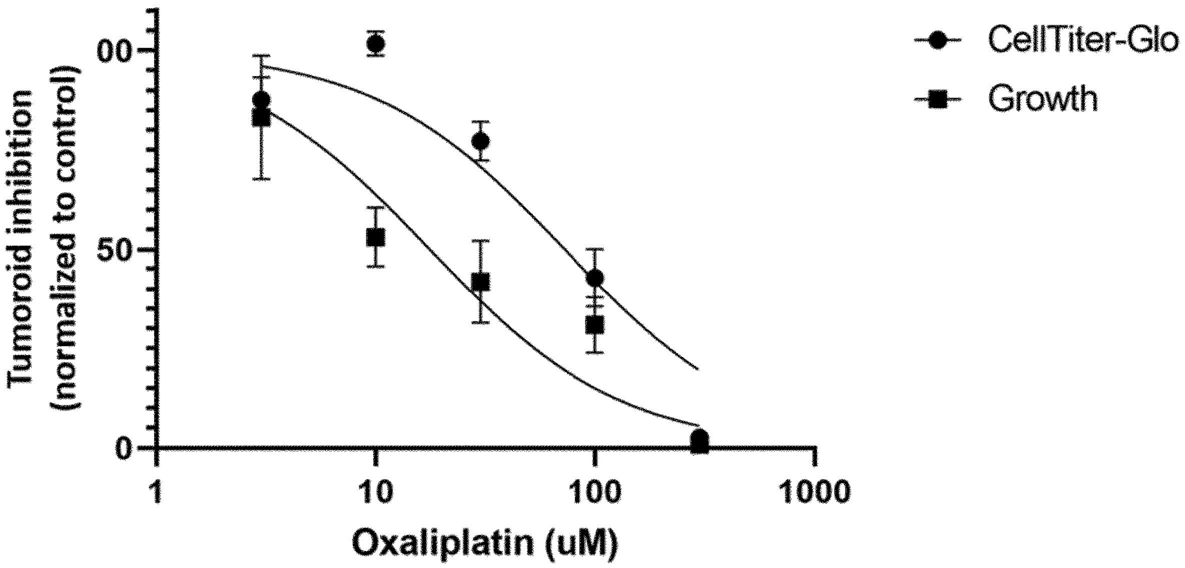
FIG. 2 shows comparison of tumoroid inhibition measured as relative growth inhibition determined by measuring projected area by imaging (Growth) and as relative inhibition by measuring ATP content using CellTiter-Glo 3D (CellTiter-Glo) after treatment with different concentrations of Oxaliplatin as indicated in the figure. The tumoroid inhibition is normalized to non-treated control tumoroids. No inhibitory effect is presented as 100% and complete inhibition is presented as 0%.
Figure 3:
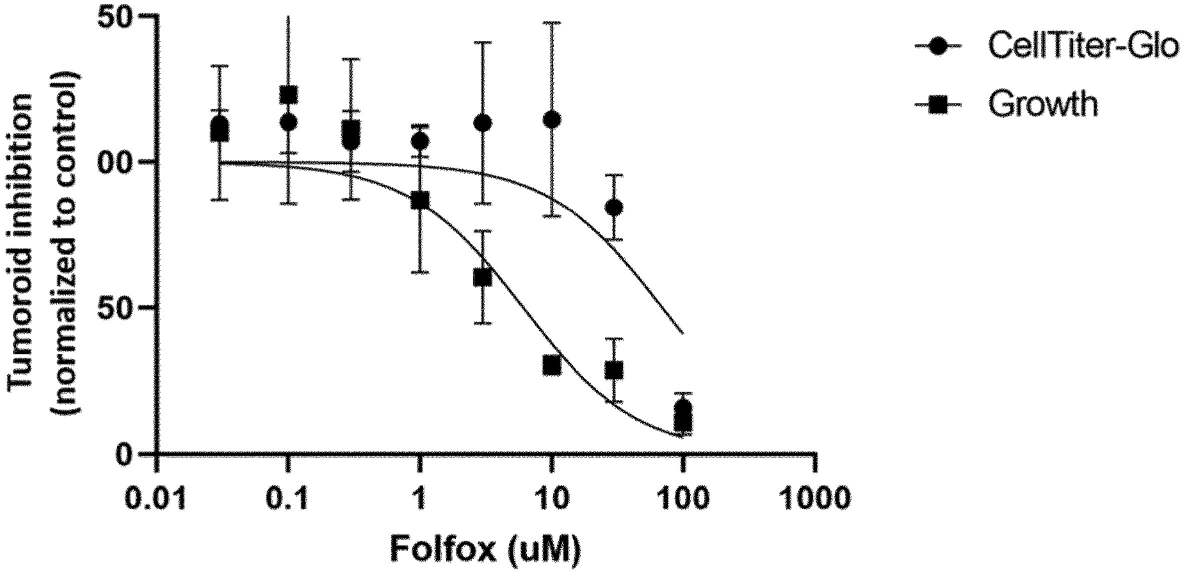
FIG. 3 shows comparison of tumoroid inhibition measured as relative growth inhibition determined by measuring projected area by imaging (Growth) and as relative inhibition by measuring ATP content using CellTiter-Glo 3D (CellTiter-Glo) after treatment with different concentrations of Folfox as indicated. The tumoroid inhibition is normalized to non-treated control tumoroids. No inhibitory effect is presented as 100% and complete inhibition is presented as 0%.
Figure 4:
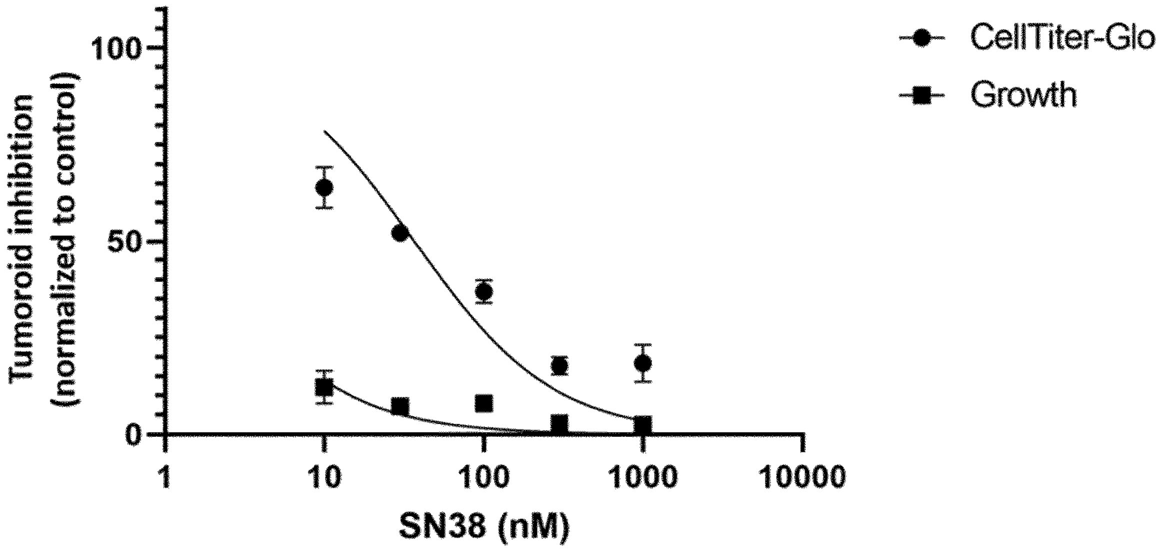
FIG. 4 shows comparison of tumoroid inhibition measured as relative growth inhibition determined by measuring projected area by imaging (Growth) and as relative inhibition by measuring ATP content using CellTiter-Glo 3D (CellTiter-Glo) after treatment with different concentrations of SN38 as indicated on the figure. The tumoroid inhibition is normalized to non-treated control tumoroids. No inhibitory effect is presented as 100% and complete inhibition is presented as 0%.

Tumoroids from four control patients were prepared, exposed to varying doses of Oxaliplatin, Folfox and SN38. Surprisingly the invention shows that inhibition of growth of the tumoroids is a significantly more sensitive measure than the measurement of change in ATP content. The results are shown in FIGS. 2 to 4. The $IC_{50}$ values (the concentration that provide a 50% inhibition of the tumoroid growth as measured with imaging and a 50% inhibition of the total ATP content released from tumor cells as measured using CellTiter-Glo) for the growth inhibition and for the ATP content are presented in Table 1.

TABLE 1

Comparison of tumoroid inhibition (IC50 values) measured with imaging (Growth) and with ATP content (CellTiter-Glo 3D) after treatment with different concentrations of Oxaliplatin, Folfox and SN38.

| | ATP (CellTiter-Glo 3D) | Growth (Imaging) |
|---|---|---|
| Oxaliplatin (uM) | | |
| IC50 | 72.73 | 17.68 |
| R squared | 0.9098 | 0.8459 |
| Folfox (uM) | | |
| IC50 | 69.83 | 6.097 |
| R squared | 0.6105 | 0.7485 |
| SN38 (nM) | | |
| IC50 | 36.68 | 1.638 |
| R squared | 0.8789 | 0.9918 |

Discussion

Surprisingly, it was found that when measuring the effect of chemotherapies like oxaliplatin, Folfox or SN38, the inhibitory effect was measured with significantly higher sensitivity when determining inhibition of growth compared to measurement of the ATP content (see FIG. 2-4 and Table 1). As shown in FIGS. 2-4 and Table 1, monitoring tumoroid inhibition after treatment with Oxaliplatin, Folfox and SN38 by determining inhibition of growth was significantly more sensitive than determining ATP content (CellTiter-Glo 3D). In this example growth was determined as projected area by Imaging. For Oxaliplatin and Folfox, inhibition of growth determined as projected area by imaging was thus between 4, 1 and 11, 5 times more sensitive than measurement of ATP content. For SN38 inhibition of growth determined as projected area by imaging was 22, 4 times more sensitive than measurement of ATP content.

REFERENCES

Cristaldi D A et al. A Reliable Flow-Based Method for the Accurate Measure of Mass Density, Size and Weight of Live 3D Tumor Spheroids. *Micromachines* 2020, 11, 465; doi:10.3390/mi11050465

Jeppesen M, Hagel G, Glenthoj A, Vainer B, Ibsen P, Harling H, Thastrup O, Jørgensen L N, Thastrup J. Short-term spheroid culture of primary colorectal cancer cells as an in vitro model for personalizing cancer medicine. *PLOS One* [*Internet*] 2017 [cited 2020 Dec. 8]; 12. Available from: https://www.ncbi.nlm.nih.gov/pmc/articles/PMC5587104/

Ooft S N, Weeber F, Dijkstra K K, McLean C M, Kaing S, van Werkhoven E, Schipper L, Hoes L, Vis D J, van de Haar J, Prevoo W, Snaebjornsson P, et al. Patient-derived organoids can predict response to chemotherapy in metastatic colorectal cancer patients. *Sci Transl Med* [*Internet*] 2019 [cited 2020 Dec. 8]; 11. Available from: pubmed.ncbi.nlm.nih.gov/31597751/

Wiederschain, G. Y. The Molecular Probes handbook. A guide to fluorescent probes and labeling technologies. *Biochemistry Moscow* 76, 1276 (2011) doi.org/10.1134/S0006297911110101).

The invention claimed is:

1. A method for predicting the efficacy of treatment of colon cancer with one or more different treatments in an individual suffering from said cancer or for predicting resistance to treatment with one or more different treatments of colon cancer in an individual suffering from said cancer, wherein each treatment is treatment with a platinum compound, said method comprising the steps of a) providing at least one colon cancer biopsy obtained from said individual, wherein the biopsy comprises or consists of colon cancer tissue from the primary colon cancer, from lymph nodes or from one or more mesastases of said colon cancer, b) dissociating the biopsy into tissue fragments comprising a plurality of cells attached to each other, c) incubating said tissue fragments in a cell-compatible support, which supports 3 dimensional maintenance and/or growth of human or other mammalian cells to generate tumoroids, wherein the cell-compatible support is a sol-gel with a sol-gel transition temperature in the range of 0 to 35° C., d) incubating a random selection of said tumoroids with the platinum compound of each treatment under conditions supporting 3 dimensional maintenance and/or growth of human or other mammalian cells, e) determining whether growth of said tumoroids is inhibited by incubation with said platinum compound, wherein inhibition of growth of said tumoroids by said platinum compound of a given treatment is indicative of efficacy of said treatment of colon cancer in said individual.

2. A method of identifying a platinum compound, which alone or in combination with one or more additional anticancer compounds are likely to be efficient in treatment of colon cancer in an individual in need thereof, said method comprising the steps of a) providing at least one colon cancer biopsy obtained from said individual, wherein the biopsy comprises or consists of colon cancer tissue from the primary colon cancer, from lymph nodes or from one or more metastases of said colon cancer, b) dissociating the biopsy into tissue fragments comprising a plurality of cells attached to each other, c) incubating said tissue fragments in a cell-compatible support, which supports 3 dimensional maintenance and/or growth of human or other mammalian cells to generate tumoroids, wherein the cell-compatible support is a sol-gel with a sol-gel transition temperature in the range of 0 to 35° C., d) providing a plurality of test combinations, wherein each test combination comprises a platinum compound, e) incubating individual random selections of said tumoroids with each of the test combinations under conditions supporting 3 dimensional maintenance and/or growth of human or other mammalian cells, and f) determining whether growth of said tumoroids is inhibited by incubation with said test combinations, wherein inhibition of growth of said tumoroids by a given test combination is indicative of efficacy of treatment of colon cancer in said individual with the platinum compound of said test combination.

3. The method according to claim 1, wherein said cancer is metastatic colon cancer.

4. The method according to claim 3, wherein the biopsy is from a metastasis.

5. The method according to claim 1, wherein at least one platinum compound is selected from the group consisting of carboplatin, cis-platin, cisplatinum, oxaliplatin and satraplatin.

6. The method according to claim 1, wherein the platinum compound is oxaliplatin.

7. The method according to claim 1, wherein one of the treatments is treatment with a combination of 5-FU, oxaliplatin and folinic acid.

8. The method according to claim 2, wherein one of the test combinations is a combination of 5-FU, oxaliplatin, SN-38 and folinic acid.

9. The method according to claim 1, wherein said biopsy is dissociated into tissue fragments each comprising a plurality of cells attached to each other.

10. The method according to claim 1, wherein the tissue fragments have a diameter of at least 30 um.

11. The method according to claim 1, wherein the majority of the tissue fragments comprises at least 10 cells attached to each other, such as in the range of 10 to 50 cells attached to each other.

12. The method according to claim 1, wherein said support is a temperature reversible gel.

13. The method according to claim 1, wherein inhibition of growth is determined by determining the volume of the tumoroids or the change in volume of the tumoroids or by determining the projected area of the tumoroids or the change in the projected area of the tumoroids or by determining the largest projected area of the tumoroids or the change in the largest projected area of the tumoroids.

14. The method according to claim 13, wherein said volume is the volume of live cells within said tumoroids and/or said area is the projected area of live cells within said tumoroids.

15. The method according to claim 1, wherein inhibition of growth is determined by determining the volume, the projected area or the largest projected area of the tumoroids or the change in volume, projected area or largest projected area of the tumoroids by imaging.

16. The method according to claim 1, wherein inhibition of growth is determined by determining the weight of the tumoroids or the change in weight of the tumoroids.

17. The method according to claim 1, wherein inhibition of growth of said tumoroids by at least 10% is indicative of efficacy or no resistance.

18. The method according to claim 1, wherein inhibition of growth is determined by determining the relative growth inhibition, wherein the relative growth inhibition is determined by a method comprising the steps of a) determining the relative growth of tumoroids incubated with the platinum compounds by determining the size of the tumoroids before and after said incubation, and dividing the size after said incubation with the size before incubation, wherein said tumroids are referred to as "test tumoroids"; and b) determining the relative growth of control tumoroids by determining the size of said control tumoroids, incubating the control tumoroids for the same amount of time and under the same conditions as the test tumoroids except that the control tumoroids are incubated in the absence of said platinum compounds and dividing the size after said incubation with the size before incubation; and c) determining the relative growth inhibition by dividing the relative growth of the test tumoroids with the relative growth of the control tumoroids wherein a low relative growth inhibition is indicative of high inhibition of growth.

19. The method according to claim 18, wherein a relative growth inhibition of less than 0.9 is considered inhibition of growth.

20. The method according to claim 1, wherein the treatment further comprises one or more additional anti-cancer compounds.

* * * * *